United States Patent
Toupy et al.

(10) Patent No.: US 11,286,230 B2
(45) Date of Patent: Mar. 29, 2022

(54) KETAMINE FLOW SYNTHESIS

(71) Applicant: Université de Liège, Liège (BE)

(72) Inventors: Thomas Toupy, Liège (BE); Romaric Gerardy, Liège (BE); Jean-Christophe Monbaliu, Esneux (BE); Diego Collin, Hannut (BE); Victor-Emmanuel Kassin, Soumagne (BE)

(73) Assignee: UNIVERSITÉ DE LIÈGE, Liège (BE)

( * ) Notice: Subject to any disclaimer, the term of this patent is extended or adjusted under 35 U.S.C. 154(b) by 0 days.

(21) Appl. No.: 16/896,909

(22) Filed: Jun. 9, 2020

(65) Prior Publication Data
US 2020/0299224 A1    Sep. 24, 2020

Related U.S. Application Data

(63) Continuation of application No. PCT/EP2018/097033, filed on Dec. 27, 2018.

(30) Foreign Application Priority Data

Dec. 29, 2017    (EP) .................................... 17211200

(51) Int. Cl.
C07C 209/80    (2006.01)
C07C 209/86    (2006.01)

(52) U.S. Cl.
CPC .......... *C07C 209/80* (2013.01); *C07C 209/86* (2013.01)

(58) Field of Classification Search
None
See application file for complete search history.

(56) References Cited

U.S. PATENT DOCUMENTS 3,254,124 A    5/1966 Stevens
2008/0268071 A1    10/2008 Gant

OTHER PUBLICATIONS

Nemethne-Sovago, J. et al. "Microreactors: A New Concept for Chemical Synthesis and Technological Feasibility (Review)" Materials Science and Engineering, vol. 39, No. 2, Jan. 1, 2014, pp. 89-101.

(Continued)

*Primary Examiner* — Sudhakar Katakam
*Assistant Examiner* — Jennifer C Sawyer
(74) *Attorney, Agent, or Firm* — Westman, Champlin & Koehler, P.A.; Z. Peter Sawicki; Amanda M. Prose

(57) ABSTRACT

The invention provides a method for synthesizing a compound of formula

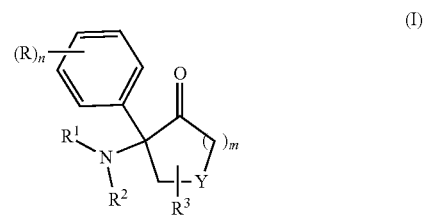

(I)

wherein each R independently represents an optionally substituted aryl, heteroaryl, alkyl, perfluoroalkyl, cycloalkyl, alkoxy, aryloxy, acyl, carboxyl, hydroxyl, halogen, amino, nitro, cyano, sulfo or sulfhydryl group, in ortho, meta or para position to the cycloalkylamine moiety; $R^1$ and $R^2$ each independently represents a hydrogen atom, a lower alkyl group or a cycloalkyl group; $R^3$ represents a hydrogen group, substituted aryl, heteroaryl, alkyl, perfluoroalkyl, (Continued)

cycloalkyl, alkoxy, aryloxy group; Y represents an oxygen atom, a sulfur atom, a NH group, a NR⁴ group or a CH₂ group;

R⁴ represents a hydrogen atom or an alkyl, aryl or a heteroaryl group; and n and m each independently represents an integer from 1 to 5; or a pharmaceutically acceptable salt thereof; or a precursor thereof; wherein the method comprises one or more of the following steps: (a) reacting a compound of formula (II)

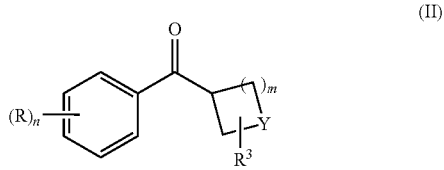

(II)

wherein R, R³, Y, n and m are as defined above in relation to the compound of formula (I) with an oxygenating agent, a first additive and a second additive in a solvent in a fluidic network or in a batch process under thermal and/or photochemical conditions to form a compound of formula (III):

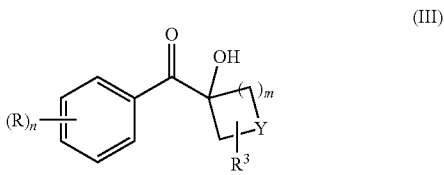

(III)

wherein R, R³, Y, n and m are as defined above in relation to the compound of formula (I), (b) reacting a compound of formula (III) with a nitrogen containing nucleophile in the presence of a third additive and/or a solvent in the fluidic network or in a batch process under thermal conditions to form a compound of formula (IV):

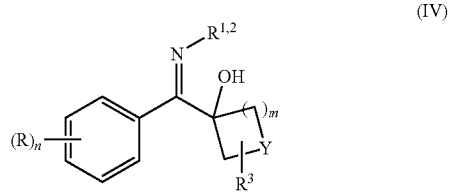

(IV)

wherein R, R₁, R₂, R₃, Y, n and m are as defined above in relation to the compound of formula (I); and/or (c) reacting a compound of formula (IV) in a fluidic network or in a batch process, optionally in the presence of a fourth additive, under thermal conditions to form a compound of formula (I); wherein one or more of steps (a), (b) and/or (c) is carried out in a fluidic network that comprises micro- and/or meso-channels having an internal dimension of from 100 μm to 2000 μm.

22 Claims, 3 Drawing Sheets

(56) References Cited

OTHER PUBLICATIONS

International Search Report issued for PCT/EP2018/097033 dated Feb. 22, 2019.
Written Opinion of the International Searching Authority issued for PCT/EP2018/097033 dated Feb. 22, 2019.
European Search Opinion issued for EP Application No. 17211200.5, dated Mar. 13, 2018.
European Search Report issued for EP Application No. 17211200.5, dated Mar. 13, 2018.
Zarantonello, P., et al. "Novel analogues of ketamine and phencyclidine as NMDA receptor antagonists" Bioorganic & Medicinal Chemistry Letters 21 (2011) 2.
European Search Report issued for EP Application No. 18839675.8, dated Sep. 28, 2020.

KETAMINE FLOW SYNTHESIS

CROSS-REFERENCE TO RELATED APPLICATION

This Application is a Bypass Continuation of International Application No. PCT/EP2018/097033, filed Dec. 27, 2018 and published as WO/2019/129815 on Jul. 4, 2019, in English, which claims priority to European patent application Serial No. EP17211200.5, filed Dec. 29, 2017, the contents of which are hereby incorporated by reference in their entirety.

The present invention relates to an improved process for the atom-economic preparation of libraries of significant arylcycloalkylamine derivatives, or intermediates thereof.

Significant arylcycloalkylamine derivatives include phenylcyclidine 0 and ketamine rac-1.

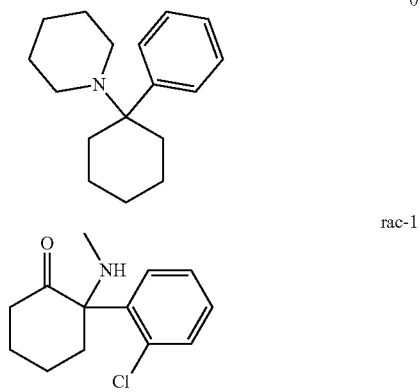

Arylcyclohexylamine derivatives are a class of important pharmaceutically active ingredients. A typical arylcyclohexylamine derivative bears a cyclohexylamine backbone featuring an aryl moiety attachment. Important characteristics of arylcyclohexylamine derivatives are (a) that the aryl moiety is in geminal position to the amine; (b) the amine is typically secondary or tertiary.

Phencyclidine is one of the first arylcyclohexylamine that was reported with recognized anesthetic properties, as well as dissociative hallucinogenic and euphoriant effects.

Ketamine belongs to the arylcyclohexylamine pharmaceutical class, and was first accepted as an ingredient for anesthetic cocktails in the late 1960s on humans and for veterinary use. Because of strong dissociative side effects, it has become a Schedule III, non-narcotic substance under the Controlled Substances Act since 1999.

Ketamine is now considered as a breakthrough medication for treating major depressive disorders with imminent risk for suicide, and is listed on the World Health Organization (WHO) list of essential medicines. According to WHO, depression will become the second cause of disability by 2020, after cardiovascular diseases. Today, the global burden of depression is a major public health challenge, both at the social and economic levels. Despite the availability of various antidepressants, several weeks, if not months, are necessary to be effective on patients. Ketamine, on the contrary, is effective after the first intake (M. W. Tyler et al., ACS Chem. Neurosci. 2017, 8, 1122).

Ketamine, (also known as 2-(2-chlorophenyl)-2-(methylamino)-cyclohexanone) bears one stereogenic center that accounts for 2 enantiomers, namely, (S)-2-(2-chlorophenyl)-2-(methylamino)-cyclohexanone (a.k.a. Esketamine, referred to herein as the compound of formula 1a) and (R)-2-(2-chlorophenyl)-2-(methylamino)-cyclohexanone (a.k.a. Arketamine, referred to herein as the compound of formula 1b).

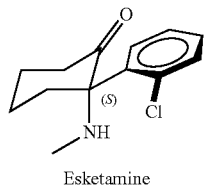

Esketamine

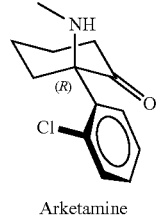

Arketamine

The most active enantiomer of ketamine is 1a, although there is still much debate regarding the intimate mechanism of action leading to its antidepressant activity. The pharmacology profile of ketamine is complex and not completely resolved yet. According to Tyler et al., ketamine acts on the central nervous system (CNS). It is a non-competitive glutamatergic N-methyl-D-aspartate (NMDA) receptor antagonist with moderate potency. The (S)-enantiomer 1a is more potent ($IC_{50}$: 465 nM) than the (R)-enantiomer 1b ($IC_{50}$: 1.340 nM).

The most common pharmaceutical formulation of ketamine consists of an aqueous solution of the racemate as a hydrochloride salt (Ketalar, Calypsol, Vetalar). Eskatemine 1a is also sold as an aqueous solution of its hydrochloride under the brand name Ketanest.

Ketamine is exclusively produced in batch, according to stepwise, time-consuming processes that use environmentally harmful/unsafe conditions or reagents.

A variety of methods have been reported in the art for the preparation of ketamine. Some of these methods afforded the racemate. "Racemate" refers to a 50:50 mixture of enantiomer 1a and 1b, without discrimination. For instance, the original procedure reported in the early 1960s by C. L. Stevens (U.S. Pat. No. 3,254,124), involves 4 different steps that are typically run sequentially, in temporally and spatially disconnected macroscopic batch reactors. This sequence of reactions is particularly long (over 7 days from advanced starting material 2), and prone to many side reactions (Scheme 1). Step 1 involves the bromation of intermediate 2, typically with N-bromosuccinimide or bromine, benozyl peroxide and carbon tetrachloride. Although alternative methods using copper salts were reported, (Gant, T. G. U.S. Pat. No. 7,638,651 B2) this step generates a considerable amount of waste, and the resulting bromoketone 3 is reported as instable. Bromoketone 3 is next reacted with pure methylamine at room temperature leading to hydroxyimine 4a. The latter step is time consuming (5 days), and comes with major impurities that require extensive purification. One of the main impurities (4b) corresponds to formula (2), and it affects drastically the purity of 1. Step 3 involves the thermolysis of 4a toward the formation of rac-1 in refluxing decalin (b.p. 186° C.) or in refluxing dichlorobenzene (b.p. 180° C.) for 2 h. Step 4 aims at the formation of the hydrochloric salt rac-1.HCl. Steps 3 and 4 can be combined (step 3') upon thermolysis of 4a in the presence of an acid, such as HCl. Steps 2 and 3 lead to significant impurities. Step 3 is very sensitive to reaction time and temperature. The presence of impurity 4b negatively affects the thermolysis step.

decomposition or give rise to side reactions, hence impacting the final purity. These methods also come with shortcomings associated to trace contamination of the final product with toxic metals. These methods use environmental unfriendly conditions, noxious reagents and solvents. These methods use stepwise macroscopic batch processes, which come with various shortcomings inherent to the technology, such as poor mixing and heat transfer, which ultimately

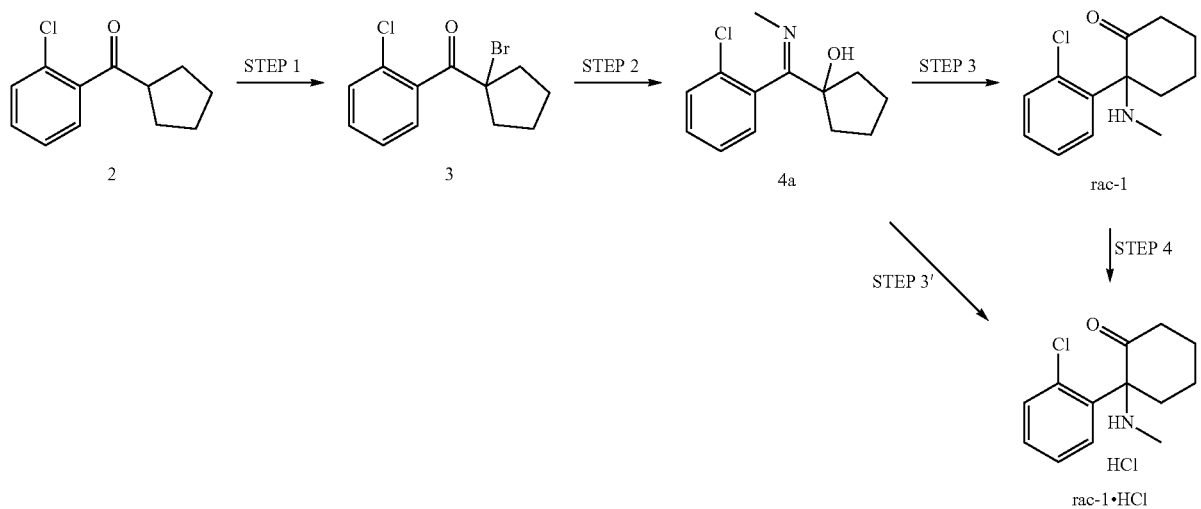

Scheme 1. Classical (prior art) sequence toward the preparation of rac-1•HCl (2)

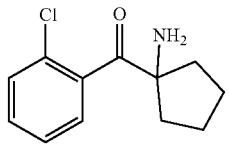

4b

More recently, a copper-assisted method utilizing ammonium nitrate for the direct nitration of cyclic ketones was reported by Zhang Z. Q et al in Org. Lett 2017, 19 (5), 1124-1127. The method was also applied for the preparation of racemic ketamine (rac-1), with an overall isolated yield of 25% (3 steps).

Other methods were dedicated to the enantioselective preparation of 1a or 1b. Some methods use expensive metal catalysts or organocatalysts combined with time-consuming multistep sequences, affording ketamine with combined yields ranging from 21 to 30% overall and enantiomeric excesses of up to 99%. For instance, Yokoyama et al. (Tetrahedron 2009, 65 (27), 5181-5191) reported in 2009 an asymmetric synthesis of esketamine 1a according to 10 steps in 21% overall yield (99% ee). In 2015, Toste et al. (J. Am. Chem. Soc. 2015, 137 (9), 3205-3208) reported a procedure for the direct asymmetric amination of α-substituted ketones with di-tert-butyl azodicarboxylates catalyzed by a chiral organophosphoric acid. Esketamine 1a was obtained accordingly in 30% overall yield (99% ee).

These methods reported in the art come with shortcomings associated with poor global efficiency (low yield) and poor atom-economy (lots of waste). Some of these methods use unstable chemical intermediates, which are prone to account for low productivity, quality deficiency and poor flexibility. A high chemical risk is associated with classical large scale, stepwise batch processes, in particular for multistep sequences involving high temperatures and/or strong oxidizers in conjunction with flammable organic solvents. Batch reactors also come with internal temperature gradients that are deleterious for chemical processes using sensitive substrates. Poor thermal control on such processes leads to low purity profiles, hence increasing process costs with extensive purifications.

A way of ameliorating these problems has been sought.

According to the invention there is provided a method for synthesizing a compound of formula

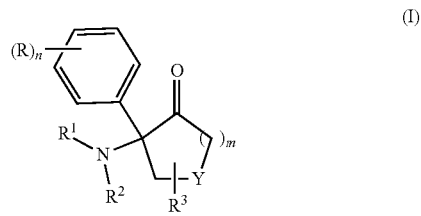

(I)

wherein each R independently represents an optionally substituted aryl, heteroaryl, alkyl, perfluoroalkyl, cycloalkyl, alkoxy, aryloxy, acyl, carboxyl, hydroxyl, halogen, amino, nitro, cyano, sulfo or sulfhydryl group, in ortho, meta or para position to the cycloalkylamine moiety;

$R^1$, $R^2$, and $R^3$ each independently represent a hydrogen atom, a lower alkyl group or a cycloalkyl group;

Y represents an oxygen atom, a sulfur atom, a NH group, a $NR^4$ group or a $CH_2$ group;

$R^4$ represents a hydrogen atom or an alkyl, aryl or a heteroaryl group; and n and m each independently represent an integer from 1 to 5; and or a pharmaceutically acceptable salt thereof; or a precursor thereof; wherein the method comprises one or more of the following steps:

(a) reacting a compound of formula (II)

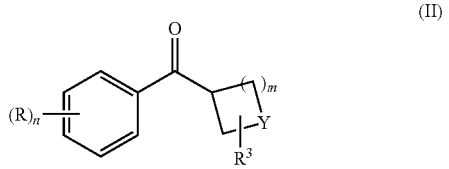

(II)

wherein R, $R^3$, Y, n and m are as defined above in relation to the compound of formula (I) with an oxygenating agent, a first additive, and a second additive in a solvent in a fluidic network or in a batch process under thermal and/or photochemical conditions to form a compound of formula (III):

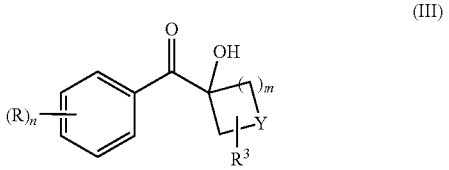

(III)

wherein R, $R^3$, Y, n and m are as defined above in relation to the compound of formula (I), (b) reacting a compound of formula (III) with a nitrogen containing nucleophile in the presence of a third additive and/or a solvent in the fluidic network or in a batch process under thermal conditions to form a compound of formula (IV):

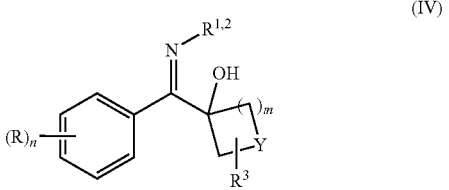

(IV)

wherein R, $R_1$, $R_2$, $R_3$, Y, n and m are as defined above in relation to the compound of formula (I); and/or (c) reacting a compound of formula (IV) in a fluidic network or in a batch process, optionally in the presence of a fourth additive, under thermal conditions to form a compound of formula (I); wherein one or more of steps (a), (b) and/or (c) is carried out in a fluidic network that comprises one or more micro- and/or meso-channels having an internal dimension of from 100 μm to 2000 μm.

The present invention significantly reduces the impurity profile, the environmental footprint and the costs associated with conventional processes toward significant arylcycloalkylamine derivatives.

A significant arylcycloalkylamine derivative is ketamine rac-1, which is defined a compound of formula I wherein R represents a chlorine atom in ortho position to the cycloalkyl moiety, $R^1$ represents a methyl group, $R^2$ represents a hydrogen atom, $R^3$ represents a hydrogen atom, Y represents a $CH_2$ group, n represents 1, and m represents 2, and the compound is pharmaceutically formulated as a hydrochloride salt.

Advantages of performing one or more of steps (a), (b), and/or (c) in a fluidic network include:

- a low environmental footprint, and uses environment-friendly conditions;
- production of significant arylcycloalkylamine derivatives related to ketamine in high overall yields and excellent purity;
- accurate control on the reaction conditions, such as a control of the temperature, the pressure, the irradiation time, the flow rate and the local stoichiometry;
- allows to quickly expose chemicals to high reaction temperatures without the formation of deleterious temperature gradients:
- permits to obtain a product with a constant quality and purity profile;
- enables a substantially safer handling of an oxygenating agent in the presence of flammable organic solvents at high temperature;
- provides a scalable, safe and intensified continuous-flow process towards an arylcycloalkylamine derivatives related to ketamine or a prodrug or a derivative or an intermediate thereof with high atom-economy and high efficiency;
- enables short reaction times
- the fluidic network setup may use intensified thermal conditions to accelerate the chemical processes and reactions, and at least one critical step can be alternatively performed under photochemical conditions;
- by streamlining multiple operations within the same uninterrupted fluidic reactor network comprising micro-/meso-channels, the present invention thus alleviates the handling of any of the chemical intermediates and large inventories of chemical intermediates;
- the process is amenable to the production of libraries of ketamine analogs using diverse arylcycloalkylamine precursors with various aromatic substitution, diverse (hetero)cycloalkyl fragments and various amines;
- the process further enables a productivity that can be adapted depending on the demand. Each step of the process can be run independently or conjointly in the continuous-flow micro-/meso-reactor network.

In some embodiments, one or more of the steps of the method may comprise one or more of the following steps: (i) flowing a fluid sample into a micro-/meso-channel; and/or (ii) performing an in-line purification; and/or (iii) performing an in-line analysis; and/or (iv) performing a chemical reaction in the micro-/meso-channel. It should be understood herein that a micro- and/or meso-channel is a channel which has an internal dimension of from 100 μm to 2000 μm, in which chemicals can be mixed, heated or cooled, or reacted. In some embodiments, the micro- and/or meso-channel may be of circular section such as a cylinder or a tube. In some embodiments, the micro- and/or meso-channel may integrate various elements such as static mixers.

Some steps of this method can be performed in batch to produce chemical intermediates which can next be transformed under continuous-flow conditions, such as for process steps involving high temperature or conditions that would typically be considered unsafe under batch conditions by one skilled in the art.

In some embodiments, step (a) of the method comprises reacting a compound of formula (II) with an oxygenating compound, a first additive which is a reductant and a second additive which is a base in a solvent in the fluidic network under thermal conditions to a compound of formula (III). In some embodiments, step (a) of the method comprises reacting a compound of formula (II) with an oxygenating compound, a first additive which is a reductant and a second additive which is a base for a reaction time of about 60 min or less, to produce a compound of formula (III). In some embodiments, the second additive which may be a base optionally containing a co-reagent for enhancing the performance of the reaction. In some embodiments, a co-reagent may be a reagent that is added to the system in order to cause a chemical reaction or to enhance performance of a reaction while not necessarily being consumed in the said reaction. It should be understood herein that enhancing the performance of the reaction means to increase the conversion and/or the selectivity. Whether the co-reagent needs to be included in the reaction mixture depends on the nature of the base. In some embodiments, step (a) of the method may comprise reacting a compound of formula (II) with an oxygenating compound, a first additive which is a reductant and a second additive which is a base in a substoichiometric amount in a solvent for a reaction time of about 60 min or less at a temperature of 150° C. or less, to produce a compound of formula (III). It should be understood herein that substoichiometric mean that the base is added in less than the equimolar amount (=100 mol %), for example 50% mol or less. In some embodiments, where the base is used in a substoichiometric amount, the optional co-reagent may be used with the same molar ratio (e.g. 50 mol % base, 50 mol % co-reagent). In some embodiments, step (a) of the method may comprise reacting a compound of formula (II) with an oxygenating compound with a first additive which is a reductant and a second additive which is a base in a catalytic amount in a solvent for a reaction time of about 60 min or less at a temperature of 150° C. or less, to produce a compound of formula (III). It should be understood herein that catalytic means that this base is added in an amount less than 10 mol %. In some embodiments, where the base is used in a catalytic amount, the optional co-reagent may be used with the same molar ratio (e.g. 5 mol % base, 5 mol % co-reagent). In some embodiments, the first additive which is a reductant can be added after the reaction of compound of formula (II) with an oxygenating compound in the presence of a second additive which is a base. In some embodiments, a fluidic network comprising micro- and/or meso-channels is utilized in step (a) of the method. Herein a micro-channel means a channel with an internal dimension of from 100 μm to 850 μm; micro-fluidic reactor means a reactor which comprises a network of micro-channels and various fluidic elements assembled in modules; meso-channel means a channel with an internal dimension of from 850 μm to 2000 μm; meso-fluidic reactor means a reactor which comprises a network of meso-channels and various fluidic elements assembled in modules. Reaction time may alternatively be expressed as a residence time in the fluidic network. Residence time means the actual process time under the specific process conditions (temperature, pressure, irradiation) inside the controlled environment of a micro-/meso-fluidic reactor and is generally expressed in minutes. The residence time may be calculated from the ratio of the internal volume of a fluidic reactor and the total flow rate in the fluidic reactor.

In some embodiments, step (a) of the method comprises reacting a compound of formula (II) with an oxygenating compound, and a first additive which is a reductant and second additive which contains a base and a catalyst in a solvent in the fluidic network under photochemical conditions to a compound of formula (III). In some embodiments, step (a) of the method comprises reacting a compound of formula (II) with an oxygenating compound, a first additive which is a reductant and a second additive which contains a base and a catalyst in a solvent for a reaction time of about 60 min or less, to produce a compound of formula (III).

In some embodiments, step (a) of the method comprises using a fluidic network comprising transparent micro- and/or meso-channels. Herein, a transparent micro- and/or meso-channel is a micro- and/or meso-channel constructed from a material that is fully transparent to light. In some embodiments, the material of micro- and/or meso-channel is transparent to light with wavelengths ranging from 300 to 800 nm, but more specifically from 400 to 600 nm. In some embodiments, a transparent micro- and/or meso channel may be constructed from glass, fused silica, and/or a transparent polymer.

In some embodiments, step (a) can be telescoped to subsequent process operations, such as to step (b). In some embodiments, step (a) can be telescoped to a subsequent process operation such that step (a) additionally comprises a step of an in- or off-line downstream purification including quench, liquid-liquid extraction, liquid-liquid separation, gas-liquid separation, filtration on silica gel or in-line crystallization. In some embodiments, liquid-liquid extraction requires the injection of a secondary phase, such as an additional reagent in a solvent. In some embodiments, in-line liquid-liquid or gas-liquid separation involves a membrane or a settling tank. In some embodiments, the liquid-liquid separation and the gas-liquid separation are effected at the same time. Herein, telescoping means the integration of multiple process or chemical operations within the same uninterrupted fluidic reactor network. In some embodiments, one or more steps of the method of the invention comprises in-line analysis including but not restricted to in-line IR monitoring or other spectroscopic methods for process monitoring purposes.

In some embodiments, step (b) comprises an imination reaction. In some embodiments, step (b) may have a yield of more than 50%. In some embodiments, step (b) may have a yield of more than 90% within a reaction time of less than 10 min, and typically less than 2 min at a reaction temperature of less than 150° C., such as less than 100° C. or more specifically 60° C. In some embodiments, step (b) uses a fluidic network comprising micro- and/or meso-channels. In some embodiments, step (b) comprises use of a third additive which is a dehydration reactant. In some embodiments, a dehydrating reactant may be a dehydrating solvent. In some embodiments, step (b) is performed in a dehydrating solvent. An example of dehydrating reactant is a co-reactant such as triethylorthoformate, sulfuric acid, or a trialkyl borate such as triethyl or triisopropyl borate and/or a solvent such as absolute ethanol (or anhydrous ethanol).

In some embodiments, step (b) can be telescoped to subsequent process operations, such as to step (c). In some embodiments, step (b) may be telescoped to a subsequent process operation such that step (b) additionally comprises a step of an in- or off-line downstream purification including quench, liquid-liquid extraction, liquid-liquid separation, or gas-liquid separation. In some embodiments, in-line liquid-liquid or gas-liquid separation involves a membrane or a settling tank. In some embodiments, the liquid-liquid separation and the gas-liquid separation are effected at the same time.

In some embodiments, step (b) of the method is performed for a reaction time of about 60 min or less. Reaction time may alternatively be expressed as a residence time in the fluidic network.

In some embodiments, step (b) can be telescoped to subsequent chemical operations, including chemical reactions, such as step (c). In some embodiments, the method comprises a continuous-flow method for synthesizing a compound of formula (I). In some embodiments, the method of the invention includes flowing a fluid sample comprising a compound of formula (IV) into a micro-/meso-channel; and/or performing an in-line purification of the compound of formula (IV); and/or performing an in-line analysis of the compound of formula (IV); and/or performing a chemical reaction, in the micro-/meso-channel, to convert the compound of formula (IV) to the compound of formula (I).

In some embodiments, step (c) comprises a thermal rearrangement reaction. It should be understood herein that a thermal rearrangement means that step (c) includes heating a compound of formula (IV) at a temperature above room temperature in a solvent. In some embodiments, the thermal rearrangement may use heating at a temperature above 100° C., and more specifically above 150° C. In some embodiments, step (c) may have a yield of more than 50%. In some embodiments, step (c) may have a yield of more than 80% within a reaction time of less than 30 min, and typically less than 15 min. In some embodiments, step (c) uses a fluidic network comprising micro- and/or meso-channels. In some embodiments, step (c) requires a fourth additive such as a homogeneous Brønsted or a Lewis acid. In some embodiments, step (c) may comprise an additive such as a heterogeneous Brønsted or Lewis acid. In some embodiments, the fourth additive combines both heterogeneous Brønsted and Lewis acidic sites such as, but not restricted to, Montmorillonite K10 or other clays. In some embodiments, step (c) is performed in the same solvent as for steps (a) and/or (b). In some embodiments, the products or effluents of steps (a) and (b) can be utilized directly for performing step (c), that is, without intermediate purification. In some embodiments, step (c) may be performed in an aprotic non-polar solvent such as toluene or decalin. In some embodiments, the effluent of step (c) may be collected in a batch surge containing a pharmaceutically acceptable acid.

In some embodiments, a fluidic network comprising micro- and/or meso-channels may be utilized in step (c) of the method. In some embodiments, a fixed bed reactor may be utilized in step (c). it should be understood herein that a fixed-bed reactor is a column with a much larger diameter than a conventional fluidic reactor (>2000 μm) that is packed with a solid catalyst. In some embodiments, the fixed-bed reactor may be packed with Montmorillonite K10 and/or another clay. In some embodiments, the fourth additive may have a specific granulometry. It should be understood herein that granulometry is the measurement of the size distribution in a collection of particles. In some embodiments, the fourth additive may have a specific granulometry of 0.5-1.25 mm. In some embodiments, the fourth additive may have a specific granulometry of <0.5 mm.

In some embodiments, step (c) can be telescoped to subsequent process operations, such that step (c) additionally comprises a step of an in- or off-line downstream purification including quench, liquid-liquid extraction, liquid-liquid separation, gas-liquid separation, filtration on silica gel, in- or off-line crystallization.

In some embodiments, step (c) can be telescoped to subsequent chemical transformations including:

(i) reaction of a compound of formula (I) with a pharmaceutically acceptable acid to form a pharmaceutically acceptable salt of a compound of formula (I), or an analog thereof; and/or (ii) a reaction of a compound of formula (I) with an organic and/or inorganic base or acid to increase the amount of a specific stereoisomer of the compound of formula (I), such as Esketamine (1a).

In some embodiments, step (c) of the method is performed for a reaction time of about 60 min or less. Reaction time may alternatively be expressed as a residence time in the fluidic network. In some embodiments, step (c) (i) of the method is performed for a reaction time of about 30 min or less. In some embodiments, steps (c) (ii) of the method of the invention are performed for a reaction time of about 60 min or less. Reaction time may alternatively be expressed as a residence time in the fluidic network.

In some embodiments, step (b) and (c) of the method are combined and performed simultaneously for a reaction time of about 60 min or less in the same fluidic network comprising micro- and/or meso-channels.

In some embodiments, step (c) can be telescoped to subsequent process operations. In some embodiments, step (c) additionally comprises a step of an injection of a solution comprising a pharmaceutically acceptable acid to react with a free base of formula (I), such that a salt of the said acid and the compound of formula (I) is formed. In some embodiments, step (c) additionally comprises a step of an injection of antisolvent in a section of fluidic network comprising a micro- and/or meso-channel to crystallize a pharmaceutically acceptable acid to form a salt of a compound of formula (I), or an analog thereof. Herein, it should be understood that an antisolvent is a solvent in which a salt of a compound of formula (I) is less soluble. A solvent/antisolvent mixture is a component for obtaining crystals. In some embodiments, the effluent of step (c) is collected in a batch surge, and the antisolvent is added afterwards. In some embodiments, (c) can be telescoped to a step that comprises flowing a salt of a compound of formula (I) in a section of fluidic network comprising a micro- and/or meso-channel in which the temperature is decreased from an initial value to a target lower temperature. In some embodiments, the initial value is the process temperature of step (c), and the target lower temperature is from 100° C. to −25° C., for example from 50° C. to 5° C. The purpose of the process of decreasing the temperature is to create a supersaturation, and is known by one skilled in the art as cooling crystallization. In some embodiments, the effluent of step (c) is collected in a batch surge, and the cooling crystallization is performed afterwards.

In some embodiments, in step (c) the solvent used is an alcohol in which the solubility of a pharmaceutically acceptable salt of a compound of formula (I) can be altered either by cooling or by adding an antisolvent. In some embodiment the pharmaceutically acceptable salt of a compound of formula (I) is a hydrochloride salt. In some embodiments, the antisolvent is an ether (such as a dialkyl ether) or an oxygenous heterocycle (such as, but not restricted to, tetrahydrofuran, 2-methyl tetrahydrofuran or 1,4-dioxane), or an alkane (such as, but not restricted to, hexane or heptane), or a cycloalkane (such as, but not restricted, cyclohexane). In some embodiments, the ratio by volume of antisolvent to solvent may range from 1:1 to 1:10, for example from 1:1 to 1:3.

In some embodiments, the method of invention may be performed using a fully telescoped system. A fully telescoped system comprises a series of micro- and/or meso-reactors which perform the steps of the method of the invention in sequence, without any interruption or isolation or handling of an intermediate compound. Advantages of using a fully telescoped system include that it can give:

- a compound of formula (I) as a free base in at least 50% isolated yield (99% conversion of the compound of formula (II)). (It should be understood that a free base is a nitrogen-containing molecule where the nitrogen atom has not reacted with a pharmaceutically acceptable acid);
- a racemic ketamine of formula 1a+1b as a free base in at least 50% isolated yield (99% conversion of the compound of formula (II);
- a pharmaceutically acceptable salt in at least 50% isolated yield (99% conversion of the starting arylcycloalkylamine precursor of formula (II) (a typical example of a pharmaceutically acceptable salt is as a hydrochloride salt); and
- a racemic ketamine of formula 1a+1b as a pharmaceutically acceptable salt in at least 50% isolated yield (99% conversion of the starting arylcycloalkylamine precursor of formula (II) (a typical example of a pharmaceutically acceptable salt is as a hydrochloride salt).

The compound of formula (II) which is the starting material of the method of the invention is available following an adapted procedure from the art, such as the one disclosed in U.S. Pat. No. 7,638,651 B2. In some embodiments, the compound of formula (II) may be prepared under a continuous-flow strategy using a flow reactor comprising micro- and/or meso-fluidic modules. In some embodiments, the compound of formula (II) may be obtained under continuous-flow conditions by adapting the known batch procedures. In some embodiments, the conditions may require solids packed in column reactors.

In some embodiments, the oxygenating agent used in the method of the invention may be gaseous dioxygen. In some embodiments, the oxygenating agent used in the method of the invention may be a solvent saturated in dioxygen. In some embodiments, the oxygenating compound may be air. In some embodiments, the oxygenating agent used in the method of the invention may be a peroxide, such as hydrogen peroxide.

In some embodiments, a suitable first additive is a reductant such as an inorganic or an organic reductant. Suitable examples of organic reductants include, but are not restricted to, an aryl or alkyl phosphine (such as triphenylphosphine or tris(2-carboxyethyl)phosphine), a phosphite (such as trimethylphosphite or triethylphosphite), or a sulfide (such as glutathione, cysteine, methionine, dithiothritol or a derivative thereof). Suitable examples of an inorganic reductant include, but are not restricted to, a sulfite or metabisulfite derived from an alkaline or alkaline earth metal. A typical example may include sodium or potassium sulfite.

In some embodiments, a second additive may be a base such as an inorganic or an organic base where step (a) is carried out under thermal conditions. Suitable examples of an organic base include, but are not restricted to, an alkoxide (such as potassium tert butoxide or sodium ethoxide), trialkylamine (such as trimethylamine or diisopropylethylamine), tetralkylammonium hydroxide (such as tetramethyl ammonium hydroxide or tetrabutyl ammonium hydroxide), guanidine (such as tetramethylguanidine or Barton's base), 1,8-diazabicycloundec-7-ene (DBU) and/or a different nitrogenous heterocyclic base, or a phosphazene-type base. Suitable examples of an inorganic base include, but are not restricted to, carbonates or hydroxides derived from alkaline or alkaline earth metals. A typical example may include potassium or cesium hydroxides, or the corresponding carbonates. In some embodiments, the base optionally contains a co-reagent for enhancing the performance of the reaction. In some embodiments, a suitable co-reagent is a metal cation ligand or scavenger. Suitable examples of metal cation ligand or scavenger include but are not restricted to ethylene glycol, glycerol or derivatives, a glycol ether (such as ethylene glycol monomethyl ether or dimethoxyethane), a cryptand (such as 1,10-diaza-4,7,13,16,21,24-hexaoxabicyclo[8.8.8]hexacosane), a polyethylenglycol (such as PEG-400) or a crown ether (such as 1,4,7,10,13,16-hexaoxacyclooctadecane or 1,4,7,10-tetraoxacyclododecane).

In some embodiments, a second additive may contain a base and a catalyst where step (a) is carried out under photochemical conditions. The catalyst may be a photosensitizing molecule. A photosensitizing molecule, also known as photosensitizer, is a molecule that produces a chemical change in another molecule under light irradiation with a specific wavelength. A catalyst is a component of chemical process that is used in sub-stoichiometric amounts, such as 0.01 to 50 mol %, and preferably between 0.1 and 5 mol %. Suitable photosensitizing molecules include, but are not restricted to, Eosine Y, Methylene Blue, a porphyrine and a derivative thereof. In some embodiments, a suitable catalyst is Rose Bengal or a derivative thereof. In some embodiments, the catalyst may be homogeneous or heterogeneous wherein a homogenous catalyst is a catalyst that is completely soluble in the reaction mixture and a heterogeneous catalyst may be a homogenous catalyst covalently anchored on an insoluble substrate such as a nano- or micrometric particle composed of silica, titania, or a polymeric material. In some embodiments, the catalyst may be anchored or coated on an internal wall of a micro- and/or meso-fluidic module. In some embodiments, the heterogeneous catalyst may be fed into a reactor with the reaction mixture as a slurry or a stable colloidal solution.

In some embodiments, the method of the invention may use a protic polar solvent such as a lower alkyl alcohol. In some embodiments, steps (a)-(c) may use the same solvent. In some embodiments, steps (a)-(c) may be carried out in different solvents. In some embodiments, the solvent remains unaltered in steps (a)-(c). In some embodiments, the method of the invention comprises performing steps (a) to (c) using the same flow of solvent which carries the various chemical intermediates through a flow reactor comprising micro- and/or meso-fluidic modules, where the solvent has a high solubility of the chemicals in the flow. In some embodiments, the solvent provides a concentration of from 0.01 to 9 mol/L, for example from 0.1 and 2 mol/L. In some embodiments, the solvent may be ethanol. In some embodiments, a binary mixture of protic polar and aprotic polar solvents can be used. Suitable aprotic polar solvents include, but are not restricted to, propylene carbonate, dimethylformamide, and/or dimethylsulfoxide. Suitable binary solvent mixtures have a composition volume ratio ranging from 1000:1 to 1:1 protic/aprotic. In some embodiments, the aprotic polar solvent component may be a co-reactant. In some embodiments, the method of the invention may comprise a fifth additive which increases solubility of the second additive which is a base. In some embodiments, the fifth additive may be a phase transfer catalyst. Acceptable phase transfer catalysts include a quaternary ammonium salt, such as tetrabutylammonium chloride, or trioctylmethylammonium chloride. In some embodiments, the phase transfer catalyst may be used in an amount from 0.01 mol % to 50 mol %, for example from 1 mol % to 15 mol % with reference to a limiting reactant. It should be understood herein that the limiting reactant is the reference reagent (typically said in default (in mol), while the other stoichiometric reagents are in excess). In some embodiments, the limiting regent may be used in an amount of one molar equivalent; in comparison a reagent in excess is used in an amount of more than one equivalent.

In some embodiments, steps (a), (b) and (c) of the method of the invention may be telescoped by using a direct oxygenation of a compound of formula (II) with mixing under thermal conditions with a nitrogen-containing nucleophile. It has surprisingly been found that such a method directly yields a compound of formula (I).

In some embodiments, steps (a), (b) and (c) of the method of the invention may be telescoped by using photochemical oxygenation of a compound of formula (II) with mixing under thermal conditions with a nitrogen-containing nucleophile. It has surprisingly been found that such a method directly yields a compound of formula (I).

Herein "acyl" means a moiety of formula —C(O)—$R^5$ where $R^5$ represents a hydrogen atom or an alkyl, cycloalkyl or aryl group. "Amino" means a moiety of formula —$NR^6R^7$ where each of $R^6$ and $R^7$ independently represents a hydrogen atom or a lower alkyl group. "Alkoxy" means a moiety of formula —$OR^8$ where $R^8$ represents an alkyl group. In some embodiments, an alkoxy group may be a methoxy group (—$OCH_3$). "Alkyl" means a monovalent optionally substituted saturated straight- or branched-chain hydrocarbon group containing from 1 to 8 carbon atoms. In some embodiments, each alkyl group may, optionally, be substituted with one or more amino, hydroxyl or sulfhydryl groups. "Perfluoroalkyl" means a monovalent optionally substituted saturated straight- or branched-chain alkyl group containing from 1 to 8 carbon atoms in which every hydrogen has been replaced by a fluorine. "Aryl" means a monovalent optionally substituted mono-, bi- or tricyclic aromatic hydrocarbon group having from 6 to 14 ring carbon atoms; for example a phenyl group. "Aryloxy" means a group of formula —$OR^9$ wherein $R^9$ represents an aryl group. In some embodiments, an alkoxy group may be phenoxy. "Carboxyl" means a moiety of formula —C(O)$OR^{10}$ wherein $R^{10}$ represents a hydrogen atom or an alkyl, cycloalkyl or aryl group. "Cycloalkyl" means a saturated optionally substituted monovalent mono- or bicyclic hydrocarbon moiety of from 3 to 10 ring carbon atoms. In some embodiments, the cycloalkyl moiety contains from 4 to 8 ring carbon atoms, for example cycloalkyl may be cyclohexyl. "Halogen" means a chlorine, fluorine, bromine or iodine atom. In some embodiments, halogen may be a chlorine or bromine atom. "Heteroaryl" means a monovalent monocyclic or bicyclic aromatic moiety of from 5 to 12 ring atoms containing one, two, or three ring heteroatoms each of which is independently selected from a nitrogen, oxygen, and/or sulfur atom, where the remaining ring atoms are each a carbon atom. "Hydroxyl" means a —OH moiety. "Lower alkyl" means a saturated optionally substituted straight- or branched-chain hydrocarbon containing from 1 to 4 carbon atoms. In some embodiments, lower alkyl means a methyl moiety. "Nitro" means a —$NO_2$ group. "Cyano" means a —CN group. "Sulfhydryl" means a —SH group. "Sulfo" means a —$SO_3H$ group. "Nitrogen-containing nucleophile" means any primary or secondary amine bearing alkyl, cycloalkyl or aryl moieties. "Prodrug" means any compound which releases a compound of formula (I) related to ketamine in vivo when such prodrug is administered to a mammal. In some embodiments, a prodrug of a compound of formula (I) may be prepared by modifying one or more functional group(s) present in the compound of formula (I) such that the modified functional group(s) may be cleaved in vivo to release the corresponding compound of formula (I). For example, a prodrug may include a compound of formula (I) which has a hydroxy, amino, or sulfhydryl substituent which is bonded to a prodrug group such that the prodrug group may be cleaved in vivo to generate a compound of formula (I) having a free hydroxyl, amino, or sulfhydryl group, respectively. Examples of prodrugs include an ester or carbamate of a hydroxy functional group in a compound of formula (I). "Organic base" means any nitrogenous organic compound with basic properties such as, but not restricted to potassium tert butoxide triethylamine, N,N-diisopropylethylamine, tetramethylguanidine, 1,8-diazabicycloundec-7-ene, tetramethylammonium hydroxide, tetramethyl(tris(dimethylamino)phosphoranylidene)phosphorictriamid-Et-imin (phosphazene base $P_2Et$). "Inorganic base" means any inorganic salt derived from alkaline or alkaline earth metals with basic properties such as, but not restricted to, NaOH, KOH, CsOH, $Na_2CO_3$, $K_2CO_3$ or $Cs_2CO_3$, or a corresponding phosphates. "A reductant" means any inorganic or an organic molecules that could reduce oxygenated intermediates such as peroxides or hydroperoxides, such as, but not restricted to, triphenylphosphine or tris(2-carboxyethyl)phosphine, or trimethylphosphite, or glutathione, cysteine, methionine, dithiothreitol or derivatives thereof, sulfites or metabisulfites derived from alkaline or alkaline earth metals such as $Na_2SO_3$, $K_2SO_3$ or $Na_2S_2O_5$. "Metal cation ligand or scavenger" means any organic ligand capable of strongly chelating a metal cation, such as, but not restricted to, ethylene glycol, ethylene glycol monomethyl ether, 1,10-diaza-4,7,13,16,21,24-hexaoxabicyclo[8.8.8]hexacosane, PEG-400 or 1,4,7,10,13,16-hexaoxacyclooctadecane. Photosensitizing molecules include, but are not restricted to, Rose Bengal, Methylene Blue, porphyrine, and/or a derivative thereof. "Pharmaceutically acceptable salt" means a conventional non-toxic salt, such as a salt derived from an inorganic acid (such as hydrochloric, hydrobromic, sulfuric, phosphoric, and/or nitric acid), an organic acid (such as acetic, propionic, succinic, glycolic, stearic, lactic, malic, tartaric, citric, glutamic, aspartic, benzoic, salicylic, oxalic, and/or ascorbic acid). A pharmaceutically acceptable salt may be prepared in a conventional manner, e.g., by reacting a free base form of the compound of formula (I) with a suitable acid. "Precursor" means a compound of formula (II), a compound of formula (III), or a compound of formula (IV), In some embodiments, the method of the invention uses a fluidic network to generate intensified continuous-flow thermal conditions for synthesizing a pharmaceutically active species (such as a compound of formula (I)), or a pharmaceutically active species precursor thereof (such as a compound of formula (III) or a compound of formula (IV)) within a short reaction time such as a reaction time less than an hour, such as less than 30 minutes or less than 5 min by utilizing a temperature from room temperature to 300° C., for example from 30° C. to 280° C. (or to 260° C. or to 220° C.), and a counter pressure ranging from 1 to 200 bar, for example from 10 to 100 bar (or to 70 bar). Herein, it should be understood that the counter-pressure is a pressure that is set at a downstream part of the reactor by the operator (for example, by using a pressure regulator). It sets the entire internal pressure of the reactor at the same value, and enables, for instance, use of a higher temperature than the boiling point of a solvent under atmospheric pressure (for example ethanol can be used as a liquid at 200° C.).

In some embodiments, the present invention uses intensified continuous-flow photochemical conditions for synthesizing a pharmaceutically active species precursor (such as a compound of formula (III)) using a short reaction time such as a reaction time less than 2 hours, such as a reaction time less than 60 min by utilizing a light source emitting in the 250 to 850 nm wavelength range, for example from 350 to 600 nm, and more specifically from 450 to 540 nm and a temperature from room temperature to 100° C., for example from 20° C. to 45° C., and a counter pressure from 1 to 100 bar, for example from 2 to 20 bar.

The present invention also discloses the integration or telescoping of multiple steps, including chemical and process steps for synthesizing a pharmaceutically active species (such as a compound of formula (I)), or pharmaceutically active species precursor thereof (such as a compound of formula (III) or a compound of formula (IV)). In some embodiments, the method of the invention uses a process parameter such as a flow rate which may be from 1 µL/min to 5000 mL/min, optionally from 100 µL/min to 100 mL/min, and more specifically from 10 µL/min to 30 mL/min.

In some embodiments, the method of the invention uses a fluidic network which comprises one or more fluidic modules, each associated with a specific process step such as, but not restricted to, in-line purification, in-line analysis and a chemical transformation. In some embodiments, a fluidic module may be constructed from a material with a high tolerance to a wide range of chemicals and a good tolerance to high temperature and pressure, such as glass, specialty glass, quartz, fused silica, a perfluorinated polymer such as PFA, ETFE, PTFE, a ceramic such as silicon carbide (SiC), and/or a metal such as copper, any grade of stainless steel (SS), Hastelloy, nickel or and/or titanium. In some embodiments, the fluidic network may comprise a microfluidic module constructed from a coil of a perfluorinated polymer with at least one defined section and volume where the section is the internal diameter of the fluidic network and volume is the internal volume of at least a part of the fluidic network, optionally the volume of the entire fluidic network. In some embodiments, a section of the reactor includes a SS column packed with a heterogeneous catalyst. In some embodiments, the fluidic network reactor comprises a mesofluidic module constructed from stainless steel (SS) with at least one defined section and volume. In some embodiments, the fluidic network reactor comprises a meso-fluidic module constructed from SiC with at least one defined section and volume. In some embodiments, a fluidic module may be constructed from a transparent material, such as glass, specialty glass such as Pyrex glass, quartz or fused silica, and/or a perfluorinated polymer such as PFA, ETFE or PTFE. In some embodiments, one or more fluidic module may be constructed from a ceramic such as SiC or a metal such as SS. In some embodiments, one or more fluidic modules are constructed from a perfluorinated polymer such as PFA, ETFE or PTFE embedded in a metal tubular casing such as copper or SS tubing. In some embodiments, two or more fluidic networks may be operated in series and/or in parallel; the two or more fluidic networks may be substantially identical.

The invention is illustrated with reference to the following Figures of the accompanying drawings which are not intended to limit the scope of the claimed invention:

Figure 1:
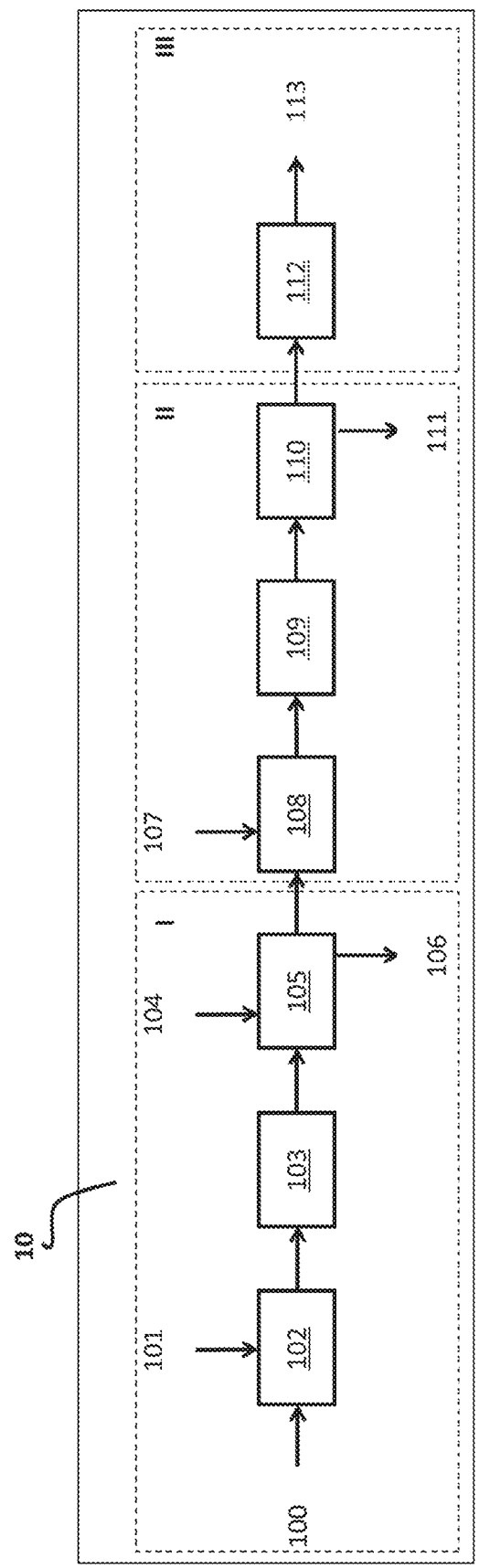
FIG. 1 shows a schematic plan view of a first embodiment of a fluidic network for use in the method of the invention.

A first embodiment of a fluidic network for use in the method of the invention is indicated generally at 10 on FIG. 1. Fluidic network 10 comprises 7 fluidic modules 102,103, 105,108,109,110,112. Fluidic modules 102,103,105,108, 109,110,112 form three distinct fluidic assemblies I, II and III. Fluidic assembly I comprises fluidic modules 102,103, 105, fluidic assembly II comprises fluidic modules 108,109, 110 and fluidic assembly III is composed of fluidic module 112. Fluidic modules 102,103,105,108,109,110,112 may be connected in series, and fluidic assemblies I, II and III can be operated as a fully telescoped process. Alternatively, assemblies I, II and III can be disconnected and run independently. The first fluidic module 102 of fluidic network 10 has two input connectors 100,101. The third fluidic module 105 of fluidic network 10 has one input connector 104 and one output connector 106. The fourth fluidic module 108 of fluidic network 10 has one input connector 107. The sixth fluidic module 110 of fluidic network 10 has one output connector 111. The last module 112 of fluidic network 10 has one output connectors 113.

The fluidic reactor network 10 comprises a first module 102 and a second module 103 fluidically connected to the first module 102, and a third module 105 fluidically connected to the second module 103 in series, and a fourth module 108 fluidically connected to the third module 105 in series, and a fifth module 109 fluidically connected to the fourth module 108 in series, and a sixth module 110 fluidically connected to the fifth module 109 in series, and a seventh module 112 fluidically connected to the sixth module 110 in series. Additional fluidic modules may be connected in series to include additional unit operations such as in-line purification, in-line analysis or chemical transformation. In some embodiments, in-line analysis includes in-line spectroscopic methods, for example in-line IR. In some embodiments, the fluidic reactor network may be duplicated and run in parallel to increase productivity. In some embodiments, the internal diameter of the fluidic reactor network can be significantly increased for increasing the productivity.

The first fluidic module 102 is dedicated to mixing two fluids which are input into module 102 by input connectors 100,101 where the two fluids contain at least a compound of formula (II) and an oxygenating agent. In an alternative embodiment, fluidic module 102 may be composed of one or more embedded mixers or one or more independent mixing elements, such as an arrow-head mixer, a T-mixer, Y-mixer, cross-junction and/or static micromixer, made either of glass, stainless steel, polymeric material and/or a ceramic material, or a membrane or a porous material, or a combination of two or more of the aforementioned materials.

The second fluidic module 103 has an integrated heat exchanger which may be operated at a temperature ranging from −10° C. to 200° C. In an alternative embodiment, a thermostat or a cryostat or any thermoregulatory device may be utilized to control the temperature of fluidic module 103. In an alternative embodiment, fluidic module 103 may have more than one section such that some sections of fluidic module 103 may be operated at different temperatures at the same time, for example at temperature above 100° C. for a first section of fluidic module 103, and below 50° C. in a last section of fluidic module 103. In an alternative embodiment, fluidic module 103 may be operated at a pressure ranging from 1 to 30 bar. In an alternative embodiment, fluidic module 103 has an integrated static mixer. In an alternative embodiment, the internal volume of fluidic module 103 may be increased by inserting an additional fluidic element. In an alternative embodiment, fluidic module 103 is constructed from a transparent material enabling the irradiation of the internal volume of fluidic module 103. In an alternative embodiment, fluidic module 103 has an integrated light source such as a fluorescent light source, low/medium/high pressure mercury vapor light, a halogen light or LEDs with appropriate wavelengths ranging from 250 to 850 nm wavelength range, for example from 350 to 600 nm, and more specifically from 450 to 540 nm.

The third fluidic module 105 is composed of an inlet for an additive fluid 104, a mixing area, a separation device, an outlet 106 for a waste stream and a back-pressure regulator on each outlet set wherein the back-pressure regulators have a cracking pressure ranging from 1 to 30 bar, for example from 5 to 15 bar. In an alternative embodiment, the additive fluid 104 contains a reductant in an appropriate solvent. The mixing area may be composed of one or more mixing elements such as an arrow-head mixer, T-mixer, Y-mixer, cross-junction or static micromixer, made either of glass, stainless steel, a polymeric material and/or a ceramic material, or a combination of two or more of the aforementioned materials. The mixing area may also be composed of a packed-bed reactor packed with beads made of an inert material such as glass, stainless steel or ceramic with a diameter ranging from 0.05 to 1 mm, for example from 0.1 to 0.2 mm. In an alternative embodiment, fluidic module 105 is composed of one or more elements for performing quench, liquid-liquid extraction, liquid-liquid separation, gas-liquid separation involving a membrane or a settling tank. In an alternative embodiment, the outlet 106 is redirected to a waste tank which contains a gas. In an alternative embodiment, in-line analysis including, but not restricted to, in-line IR monitoring or other spectroscopic methods, may be integrated in fluidic module 105. In an alternative embodiment, fluidic module 105 only regulates the upstream pressure, ranging from 1 to 30 bar, for example from 5 to 15 bar.

The fourth fluidic module 108 is dedicated to adding fluids via inlet 107 to the main organic effluent from upstream fluidic module 105, and to mixing these two fluids that contain at least a pharmaceutically active species precursor such as a hydroxylated compound of formula (III). Fluid 107 may comprise at least a nitrogen-containing nucleophile. In an alternative embodiment, fluidic module 108 may comprise an embedded mixer or an inserted independent fluidic element, such as an arrow-head mixer, T-mixer, Y-mixer, cross-junction or static micromixer, made of glass, stainless steel, polymeric material and/or ceramic.

The fifth fluidic module 109 is integrated with a heat exchanger, and may be operated at a temperature ranging from 20 to 250° C., for example from 80 to 160° C. In an alternative embodiment, a thermostat or a cryostat or other thermoregulatory device may be utilized to control the temperature of fluidic module 109. In an alternative embodiment, fluidic module 108 may comprise two or more sections such that one or more sections of fluidic module 108 may each be operated at different temperatures at the same time, for example at a temperature above 50° C. for the first section of fluidic module 109, and at a temperature below 200° C. in the last section of fluidic element 109. In an alternative embodiment, fluidic module 109 has integrated static mixers. In an alternative embodiment, the internal volume of fluidic module 109 may be increased by inserting one or more additional fluidic elements. In an alternative embodiment, fluidic module 109 may comprises an integrated back-pressure regulator having a cracking pressure setting ranging from 1 to 30 bar, for example from 4 and 15 bar. In an alternative embodiment, fluidic modules 108,109 can be disconnected from fluidic module 105, and the corresponding processes may be run independently.

The sixth fluidic module 110 integrates additional downstream operations is composed of an outlet 111 for a waste stream and a back-pressure regulator on each outlet set wherein the back-pressure regulators have a cracking pressure ranging from 1 to 30 bar, for example from 5 to 15 bar. In an alternative embodiment, fluidic module 110 is composed of one or more elements for performing quench, liquid-liquid extraction, liquid-liquid separation, gas-liquid separation involving a membrane or a settling tank. In an alternative embodiment, the outlet 111 is redirected to a waste tank which contains a gas and/or a liquid. In an alternative embodiment, in-line analysis including, but not restricted to, in-line IR monitoring or other spectroscopic methods, may be integrated in fluidic module 110. In an alternative embodiment, fluidic module 110 only regulates the upstream pressure, ranging from 1 to 30 bar, for example from 5 to 15 bar.

The seventh fluidic module 112 is integrated with a heat exchanger and a high pressure pumping system, and may be operated at a temperature ranging from 20 to 300° C., for example from 120 to 280° C. In an alternative embodiment, a thermostat or a cryostat or other thermoregulatory device may be utilized to control the temperature of fluidic module 112. In an alternative embodiment, fluidic module 112 may comprise two or more sections such that one or more sections of fluidic module 112 may each be operated at different temperatures at the same time, for example at a temperature above 100° C. for the first section of fluidic module 112, and at a temperature below 200° C. in the last section of fluidic element 112. In an alternative embodiment, the internal volume of fluidic module 112 may be increased by inserting one or more additional fluidic elements. In an alternative embodiment, fluidic module 112 may comprise an integrated back-pressure regulator having a cracking pressure setting ranging from 1 to 200 bar, for example from 20 to 100 bar. In an alternative embodiment, fluidic module 112 can be disconnected from fluidic module 110, and the corresponding processes may be run independently. In an alternative embodiment, fluidic module 112 integrates one or more additional downstream operations such as liquid-liquid extraction, liquid-liquid separation, liquid-solid separation, crystallization, mixing with another fluid containing at least one solvent, formulation, temperature control such as but not restricted to cooling, crystallization, automated collection and/or in-line analysis. Fluid 113 comprises an organic solvent, and/or a pharmaceutically active species precursor in solution and/or a pharmaceutically active species in solution and/or a formulation of pharmaceutically active species in solution. In an alternative embodiment, fluid 113 comprises a carrier fluid comprising an organic solvent, and/or organic impurities in solution, and/or a pharmaceutically active species precursor in suspension and/or a pharmaceutically active species in suspension and/or a formulation of pharmaceutically active species in suspension.

Figure 2:
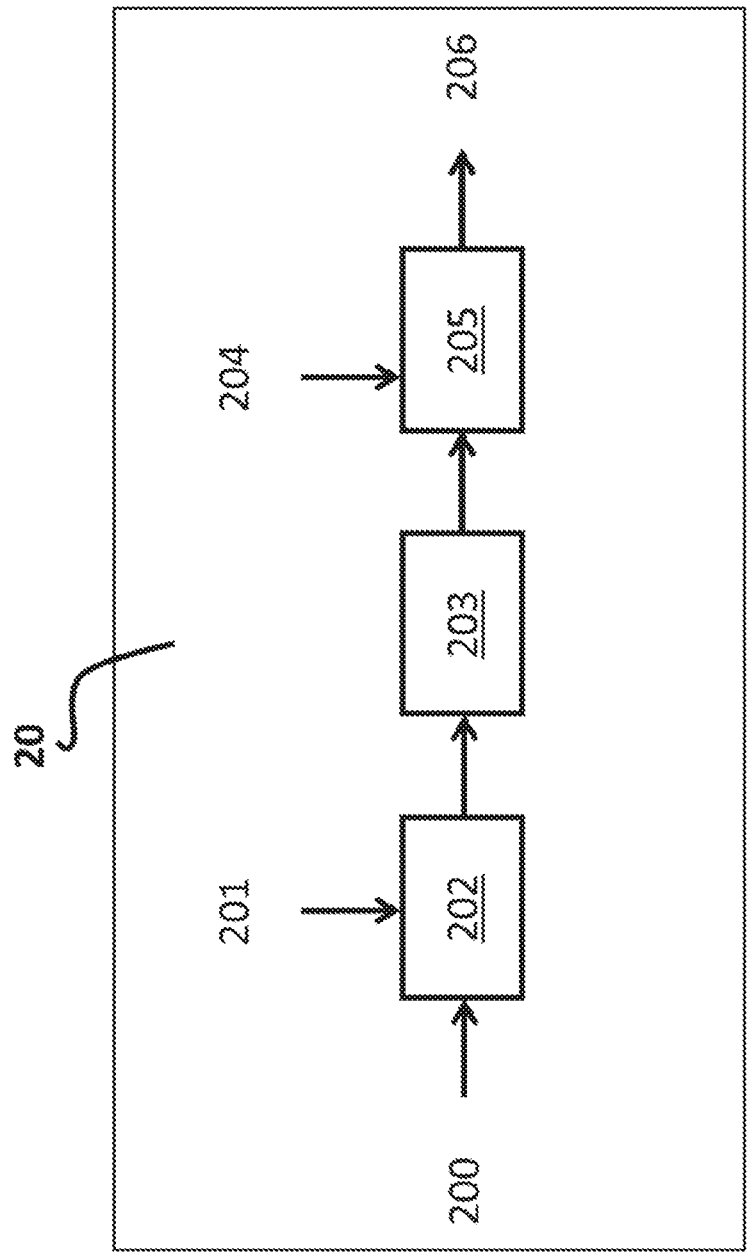
FIG. 2 shows a schematic plan view of a second embodiment of a fluidic network for use in the method of the invention.

A fluidic network according to a second embodiment of the invention for use in the method of the invention is indicated generally at 20 on FIG. 2 of the accompanying drawings. Fluidic network 20 comprises a first module 202 and a second module 203 fluidically connected to the first module 202, and a third module 205 fluidically connected to the second module 203 in series. One or more additional fluidic modules may be connected in series to include one or more additional unit operations such as in-line purification, in-line analysis or chemical transformation. In some embodiments, in-line analysis includes in-line spectroscopic methods, for example in-line IR. In some embodiments, the fluidic reactor network may be duplicated and run in parallel to increase productivity. In some embodiments, the internal diameter of the fluidic reactor network can be significantly increased for increasing the productivity.

The first fluidic module 202 is dedicated to mixing two fluids which are input into module 202 by input connectors 200,201 where the two fluids contain at least a compound of formula (IV) which is a hydroxylated imino-arylcycloalkylamine precursor and an acid in a solvent. In an alternative embodiment, fluidic module 202 may be composed of one or more embedded mixers or independent mixing elements, such as an arrow-head mixer, T-mixer, Y-mixer, cross-junction and/or static micromixer, made of glass, stainless steel, polymeric material and/or a ceramic material, or a combination of two or more of the aforementioned materials.

The second fluidic module 203 has an integrated heat exchanger which may be operated at a temperature ranging from 20 to 250° C., for example from 120 to 220° C. In an alternative embodiment, a thermostat or a cryostat or any thermoregulatory device may be utilized to control the temperature of fluidic module 203. In an alternative embodiment, fluidic module 203 may have more than one section such that some sections of fluidic module 203 may be operated at different temperatures at the same time, for example at a temperature above 100° C. for a first section of fluidic module 203, and below 250° C. in a last section of fluidic module 203. In an alternative embodiment, fluidic module 203 may be operated at a pressure ranging from 1 to 100 bar, for example from 20 to 70 bar. In an alternative embodiment, fluidic module 203 has an integrated static mixer. In an alternative embodiment, the internal volume of fluidic module 203 may be increased by inserting an additional fluidic element.

The third fluidic module 205 is composed of an inlet for an additive fluid 204, a mixing area, and a back-pressure regulator with a cracking pressure ranging from 1 to 100 bar, for example from 20 to 70 bar. In an alternative embodiment, the additive fluid 204 contains an antisolvent. The mixing area may be composed of one or more mixing elements such as an arrow-head mixer, T-mixer, Y-mixer, cross-junction and/or static micromixer, made either of glass, stainless steel, a polymeric material and/or a ceramic material, or a combination of two or more of the aforementioned materials. In an alternative embodiment, fluidic module 205 integrates one or more additional downstream operations such as liquid-liquid extraction, liquid-liquid separation, liquid-solid separation, crystallization, mixing with another fluid containing at least one solvent, formulation, temperature control such as but not restricted to cooling, crystallization, automated collection and/or in-line analysis. Fluid 206 comprises an organic solvent, and/or a pharmaceutically active species precursor in solution and/or a pharmaceutically active species in solution and/or a formulation of pharmaceutically active species in solution. In an alternative embodiment, fluid 206 comprises a carrier fluid comprising an organic solvent, and/or organic impurities in solution, and/or a pharmaceutically active species precursor in suspension and/or a pharmaceutically active species in suspension and/or a formulation of pharmaceutically active species in suspension.

Figure 3:
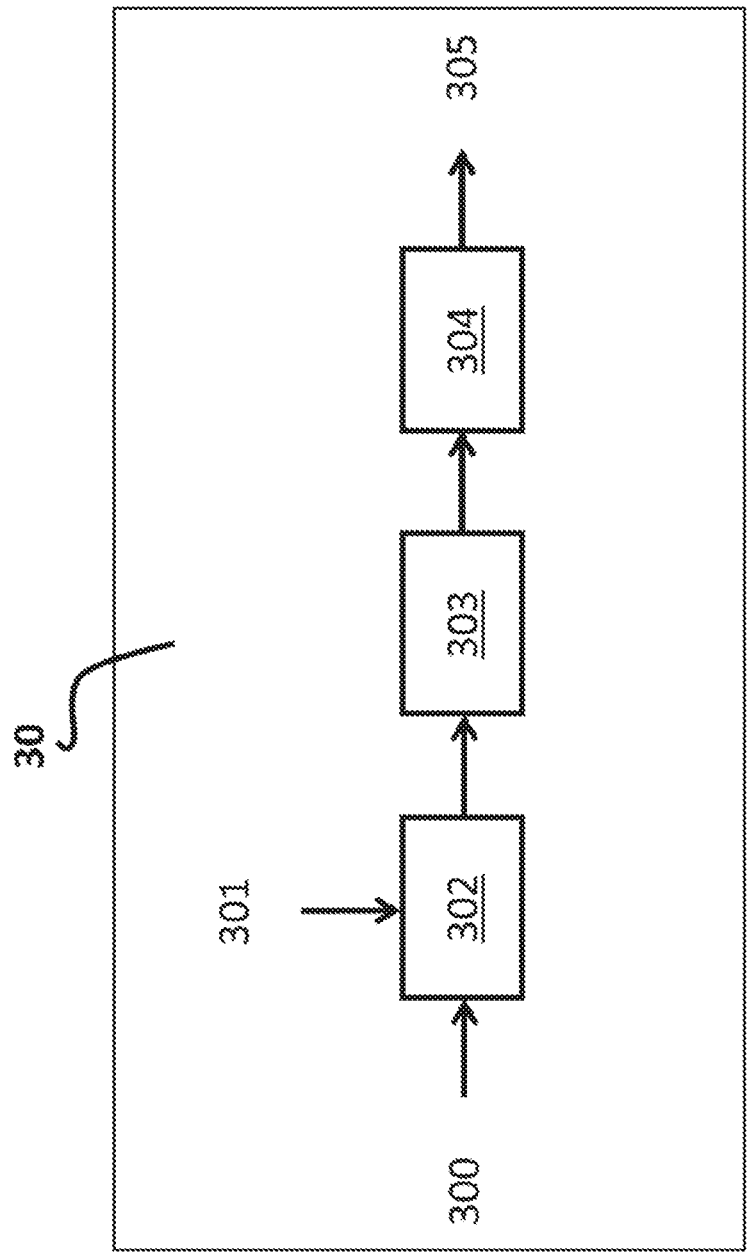
FIG. 3 shows a schematic plan view of a third embodiment of a fluidic network for use in the method of the invention.

A fluidic network according to a third embodiment of the invention for use in the method of the invention is indicated generally at 30 on FIG. 3 of the accompanying drawings. Fluidic network 30 comprises a first module 302 and a second module 303 fluidically connected to the first module 302, and a third module 304 fluidically connected to the second module 303 in series. Additional fluidic modules may be connected in series to include one or more additional unit operations such as in-line purification, in-line analysis or chemical transformation. In some embodiments, in-line analysis includes an in-line spectroscopic method, for example in-line IR. In some embodiments, the fluidic reactor network may be duplicated and run in parallel to increase productivity.

The first fluidic module 302 is dedicated to mixing two fluids which are input into module 302 by input connectors 300,301 where the two fluids contain at least a compound of formula (III) which is a hydroxylated arylcycloalkylamine precursor and a nitrogen-containing nucleophile in a solvent or a mixture of solvents. In an alternative embodiment, fluidic module 302 may be composed of one or more embedded mixers or independent mixing elements, such as an arrow-head mixer, T-mixer, Y-mixer, cross-junction and/or static micromixer, made of glass, stainless steel, a polymeric material and/or a ceramic material, or a combination of two or more of the aforementioned materials.

The second fluidic module 303 has an integrated heat exchanger which may be operated at a temperature ranging from 20 to 250° C., for example from 80 to 160° C. In an alternative embodiment, a thermostat or a cryostat or any thermoregulatory device may be utilized to control the temperature of fluidic module 303. In an alternative embodiment, fluidic module 303 may be operated at a pressure ranging from 1 to 200 bar, for example from 20 to 100 bar. In an alternative embodiment, fluidic module 303 has an integrated static mixer. In an alternative embodiment, the internal volume of fluidic module 303 may be increased by inserting an additional fluidic element.

The third fluidic module 304 has an integrated heat exchanger which may be operated at a temperature ranging from 20 to 300° C., for example from 160 to 280° C. In an alternative embodiment, a thermostat or a cryostat or any thermoregulatory device may be utilized to control the temperature of fluidic module 304. In an alternative embodiment, fluidic module 304 may be operated at a pressure ranging from 1 to 200 bar, for example from 20 to 100 bar. In an alternative embodiment, fluidic module 304 has an integrated static mixer. In an alternative embodiment, the internal volume of fluidic module 304 may be increased by inserting an additional fluidic element. In an alternative embodiment, fluidic module 304 integrates one or more additional downstream operations such as liquid-liquid extraction, liquid-liquid separation, liquid-solid separation, crystallization, mixing with another fluid containing at least one solvent, formulation, temperature control such as but not restricted to cooling, crystallization, automated collection and/or in-line analysis. Fluid 305 comprises an organic solvent, and/or a pharmaceutically active species precursor in solution and/or a pharmaceutically active species in solution and/or a formulation of pharmaceutically active species in solution. In an alternative embodiment, fluid 305 comprises a carrier fluid comprising an organic solvent, and/or organic impurities in solution, and/or a pharmaceutically active species precursor in suspension and/or a pharmaceutically active species in suspension and/or a formulation of pharmaceutically active species in suspension.

The invention will now be illustrated by reference to the following Examples which are not intended to limit the scope of the invention claimed.

EXAMPLES

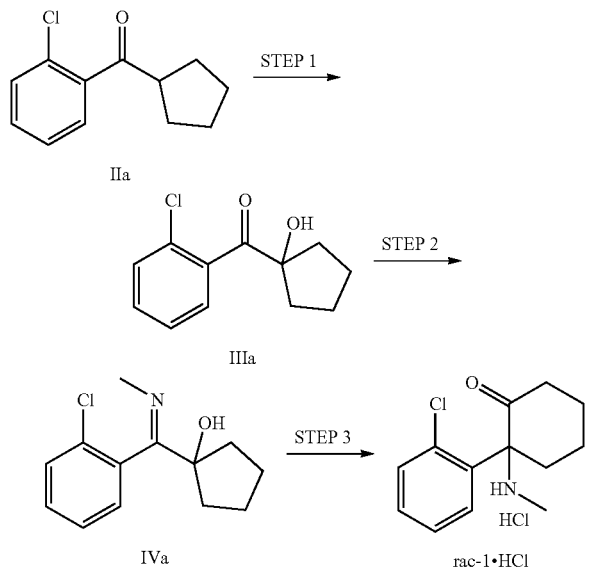

Preparative Example 1

Preparation of (2-Chlorophenyl)(Cyclopentyl)Methanone (IIa) in Batch 3.04 g (125 mmol, 1 eq.) of magnesium powder were charged in a flame-dried 500 mL round-bottom two-neck flask equipped with a condenser, and covered with 100 mL of freshly distilled diethyl ether. To the suspension were added dropwise 20.5 g (0.138 mol, 1.1 eq.) of bromocyclopentane over 1 h, and the solution was maintained at a gentle reflux upon disappearance of the magnesium. Then, a solution of 0.179 g (1.25 mmol, 0.01 eq.) of copper (I) bromide (CuBr) and 0.280 g of (1,4-diazabicyclo[2.2.2]octane) DABCO (2.5 mmol, 0.02 eq.) in 10 mL of dry diethyl ether was added in one portion to the Grignard reagent. In another flame-dried Schlenk tube, a solution of 17.2 g of 2-chlorobenzonitrile (125 mmol, 1 eq.) in 100 mL of dry diethyl ether was prepared, and next cannulated to the Grignard reagent. The resulting mixture was stirred overnight. Afterwards, the reaction mixture was cooled in an ice-bath, and 100 mL of aqueous HCl (1.2 M) were added. The solution was stirred for 6 h, and then extracted with 5×40 mL of diethyl ether. The organic extracts were washed with 50 mL of brine, dried over anhydrous magnesium sulfate, filtrated and concentrated under reduced pressure. 13.04 g of 2-chlorophenyl)(cyclopentyl)methanone (IIa) were obtained after bulb-to-bulb distillation (50% overall yield). Characterization $^1$H NMR (250 MHz, CDCl$_3$) 7.51-7.14 (m, 1H), 3.52 (p, J=7.8 Hz, 0H), 1.99-1.74 (m, 1H), 1.73-1.44 (m, 1H). $^{13}$C NMR (100.6 MHz, CDCl$_3$) 206.8, 140.3, 130.6, 29.4, 26.0.

Example 2

Preparation of (2-Chlorophenyl)(1-Hydroxycyclopentyl)Methanone (IIIa) in Batch

A flame-dried 500 mL round-bottom flask was charged with a second additive in the form of a base which is cesium carbonate (Cs$_2$CO$_3$) (3.16 g, 9.71 mmol, 0.2 eq.) and a first additive in the form of a reductant which is triethyl phosphite (P(OEt)$_3$) (16.5 mL, 96.22 mmol, 2 eq.), (2-chlorophenyl)(cyclopentyl)methanone (IIa) (10.05 g, 48.16 mmol, 1 eq.) and dimethyl sulfoxide (DMSO) (100 mL). The resulting suspension was stirred under an oxygen (O$_2$) atmosphere for 24 h at room temperature. The solution was next diluted with ethyl acetate (250 mL), washed with 200 mL of brine, extracted with ethyl acetate (3×100 mL). The resulting solution in ethyl acetate was dried over magnesium sulfate (MgSO$_4$), filtrated and concentrate under reduced pressure. The product was purified on silica gel by chromatography, and compound (2-chlorophenyl)(1-hydroxycyclopentyl)methanone (IIIa) was obtained as a pale-yellow oil (10.43 g, 96% yield, 99% conversion). Characterization $^1$H NMR (400 MHz, CDCl$_3$) 7.42 (dd, J=8.0, 1.4 Hz, 1H), 7.37 (td, J=8.0, 7.6, 1.8 Hz, 1H), 7.31 (td, J=7.4, 1.4 Hz, 1H), 7.26 (dd, J=7.5, 1.8 Hz, 1H), 3.24 (s, 1H), 2.22-2.07 (m, 2H), 2.00-1.84 (m, 4H), 1.76 (m, 2H). $^{13}$C NMR (100.6 MHz, CDCl$_3$) 209.4, 138.3, 130.7, 130.3, 129.9, 127.2, 126.4, 88.5, 39.3, 24.3. ESI: [M+Na]$^+$ calcd: 247.04963, found: 247.04961.

Example 3

Preparation of (2-Chlorophenyl)(1-Hydroxycyclopentyl)Methanone (IIIa) in Batch with Photo-Irradiation A flame-dried 500 mL round-bottom flask was charged with (2-chlorophenyl)(cyclopentyl)methanone (IIa)(10.05 g, 48.16 mmol, 1 eq.) and a second additive containing a base which is cesium carbonate (Cs$_2$CO$_3$) (3.16 g, 9.71 mmol, 0.2 eq.) and a photosensitizer which is Rose Bengal (5 mol %) and ethanol (100 mL). The resulting suspension was stirred under an oxygen (O$_2$) atmosphere for 10 h at room temperature upon irradiation at 540 nm (12 LEDs). A solution of a first additive which is a reductant in the form of triethyl phosphite (P(OEt)$_3$) (16.5 mL, 96.22 mmol, 2 eq.) in ethanol was added, and the solution was stirred for 1 h at room temperature. The solvent was removed under reduced pressure, and compound (2-chlorophenyl)(1-hydroxycyclopentyl)methanone (IIIa) was obtained in 30% conversion.

Example 4

Preparation of (2-Chlorophenyl)(1-Hydroxycyclopentyl)Methanone (IIIa) in Batch with Potassium Tert Butoxide as Second Additive A flame-dried 500 mL round-bottom flask was charged with a second additive in the form of a base which is potassium ter butoxide (KOtBu) (1.09 g, 9.71 mmol, 0.2 eq.) and a first additive in the form of a reductant which is triethyl phosphite (P(OEt)3) (16.5 mL, 96.22 mmol, 2 eq.), (2-chlorophenyl)(cyclopentyl)methanone (IIa) (10.05 g, 48.16 mmol, 1 eq.) and ethanol (100 mL). The resulting suspension was stirred under an oxygen (O$_2$) atmosphere for 24 h at room temperature. The solvent was evaporated, and the residue was diluted with ethyl acetate (250 mL), and washed with 200 mL of brine. The resulting solution in ethyl acetate was dried over magnesium sulfate ($MgSO_4$), filtrated and concentrate under reduced pressure. Compound (2-chlorophenyl)(1-hydroxycyclopentyl)methanone (IIIa) was obtained as a pale-yellow oil with 99% conversion and 27% selectivity.

Example 5

Preparation of (2-Chlorophenyl)(1-Hydroxycyclopentyl)Methanone (IIIa) in Flow with Cesium Carbonate as Second Additive A feed solution containing (2-chlorophenyl)(cyclopentyl)methanone (IIa) (0.1 M) and a second additive in the form of a base which is cesium carbonate ($Cs_2CO_3$) (20 mol %) and in ethanol containing dimethyl sulfoxide (DMSO) (5% volume) was pumped at a flow rate of 0.1 mL $min^{-1}$ and mixed with a stream of oxygen gas (10 mL·$min^{-1}$). Oxygen (AirLiquide, Alphagaz 1) and the liquid feed solution were mixed through a static mixer (T-Mixer, IDEX-Upchurch, natural PEEK 1/4-28 thread for 1/16" o.d. tubing, 0.02" through hole) placed upstream the reaction coil. The resulting reaction mixture was reacted for 15 min in the reaction coil under thermal conditions at 25° C. (room temperature). The continuous-flow setup for the oxygenation of (2-chlorophenyl)(cyclopentyl)methanone (IIa) was constructed from a high purity PFA capillary (800 μm internal diameter) wrapped in coils around a thermoregulated aluminum cylinder. A back-pressure regulator set at 250 psi was inserted downstream. The reactor effluent was collected, quenched with a first additive which is a reductant in the form of sodium metabisulfite ($Na_2S_2O_5$) and processed, affording compound (2-chlorophenyl)(1-hydroxycyclopentyl)methanone (IIIa) was obtained in 40% conversion.

Example 6

Preparation of (2-Chlorophenyl)(1-Hydroxycyclopentyl)Methanone (IIIa) in Flow with Phosphazene Base P2-Et as Second Additive A feed solution containing (2-chlorophenyl)(cyclopentyl)methanone (IIa) (1 M) a first additive in the form of a reductant which is triethyl phosphite (($P(OEt)_3$), 110 mol %) and a second additive in the form of a base which is phosphazene base $P_2$-Et ($P_2$-Et) (50 mol %) in ethanol was pumped at a flow rate of 0.2 mL $min^{-1}$ and mixed with a stream of oxygen gas (10 mL·$min^{-1}$). Oxygen (AirLiquide, Alphagaz 1) and the liquid feed solution were mixed through a static mixer (T-Mixer, IDEX-Upchurch, natural PEEK 1/4-28 thread for 1/16" o.d. tubing, 0.02" through hole) placed upstream the reaction coil. The resulting reaction mixture was reacted for 5 min in the reaction coil under thermal conditions at 25° C. The continuous-flow setup for the oxygenation of (2-chlorophenyl)(cyclopentyl)methanone (IIa) was constructed from a high purity PFA capillary (800 μm internal diameter) wrapped in coils in a thermoregulated device. A back-pressure regulator set at 160 psi was inserted downstream. The reactor effluent was collected and processed, affording compound (2-chlorophenyl)(1-hydroxycyclopentyl)methanone (IIIa) in 95% conversion (98% selectivity).

Example 7

Preparation of (2-Chlorophenyl)(1-Hydroxycyclopentyl)Methanone (IIIa) in Flow with Potassium Tert Butoxide as Second Additive A feed solution containing (2-chlorophenyl)(cyclopentyl)methanone (IIa) (1 M), a first additive in the form of a reductant which is triethyl phosphite (($P(OEt)_3$), 110 mol %) and a second additive in the form of a base which is potassium tert butoxide (50 mol %) in ethanol was pumped at a flow rate of 0.2 mL $min^{-1}$ and mixed with a stream of oxygen gas (10 mL·$min^{-1}$). Oxygen (AirLiquide, Alphagaz 1) and the liquid feed solution were mixed through a static mixer (T-Mixer, IDEX-Upchurch, natural PEEK 1/4-28 thread for 1/16" o.d. tubing, 0.02" through hole) placed upstream the reaction coil. The resulting reaction mixture was reacted for 5 min in the reaction coil under thermal conditions at 35° C. The continuous-flow setup for the oxygenation of (2-chlorophenyl)(cyclopentyl)methanone (IIa) was constructed from a high purity PFA capillary (800 μm internal diameter) wrapped in coils in a thermoregulated device. A back-pressure regulator set at 160 psi was inserted downstream. The reactor effluent was collected and processed, affording compound (2-chlorophenyl)(1-hydroxycyclopentyl)methanone (IIIa) in >95% conversion (50% selectivity).

Example 8

Preparation of (2-Chlorophenyl)(1-Hydroxycyclopentyl)Methanone (IIIa) in Flow with Potassium Tert Butoxide and 18-C-6 as Second Additive A feed solution containing (2-chlorophenyl)(cyclopentyl)methanone (IIa) (1 M), a first additive in the form of a reductant which is triethyl phosphite (($P(OEt)_3$), 110 mol %) and a second additive containing a base which is potassium tert butoxide (50 mol %) and a metal cation scavenger which is 1,4,7,10,13,16-hexaoxacyclooctadecane (18-C-6, 50 mol %) in ethanol was pumped at a flow rate of 0.2 mL $min^{-1}$ and mixed with a stream of oxygen gas (10 mL·$min^{-1}$). Oxygen (AirLiquide, Alphagaz 1) and the liquid feed solution were mixed through a static mixer (T-Mixer, IDEX-Upchurch, natural PEEK 1/4-28 thread for 1/16" o.d. tubing, 0.02" through hole) placed upstream the reaction coil. The resulting reaction mixture was reacted for 5 min in the reaction coil under thermal conditions at 30° C. The continuous-flow setup for the oxygenation of (2-chlorophenyl)(cyclopentyl)methanone (IIa) was constructed from a high purity PFA capillary (800 μm internal diameter) wrapped in coils in a thermoregulated device. A back-pressure regulator set at 160 psi was inserted downstream. The reactor effluent was collected and processed, affording compound (2-chlorophenyl)(1-hydroxycyclopentyl)methanone (IIIa) in >99% conversion (96% selectivity).

Example 9

Preparation of (2-Chlorophenyl)(1-Hydroxycyclopentyl)Methanone (IIIa) in Flow with Potassium Hydroxide as Second Additive A feed solution containing (2-chlorophenyl)(cyclopentyl)methanone (IIa) (1 M), a first additive in the form of a reductant which is triethyl phosphite ((P(OEt)$_3$), 110 mol %) and a second additive in the form of a base which is potassium hydroxide (50 mol %) in ethanol was pumped at a flow rate of 0.2 mL min$^{-1}$ and mixed with a stream of oxygen gas (10 mL·min$^{-1}$). Oxygen (AirLiquide, Alphagaz 1) and the liquid feed solution were mixed through a static mixer (T-Mixer, IDEX-Upchurch, natural PEEK 1/4-28 thread for 1/16" o.d. tubing, 0.02" through hole) placed upstream the reaction coil. The resulting reaction mixture was reacted for 5 min in the reaction coil under thermal conditions at 30° C. The continuous-flow setup for the oxygenation of (2-chlorophenyl)(cyclopentyl)methanone (IIa) was constructed from a high purity PFA capillary (800 μm internal diameter) wrapped in coils in a thermoregulated device. A back-pressure regulator set at 160 psi was inserted downstream. The reactor effluent was collected and processed, affording compound (2-chlorophenyl)(1-hydroxycyclopentyl)methanone (IIIa) in >88% conversion (64% selectivity).

Example 10

Preparation of (2-Chlorophenyl)(1-Hydroxycyclopentyl)Methanone (IIIa) in Flow with Potassium Hydroxide and with 18-C-6 as Second Additive The reaction was carried out as in Example 9 except that a metal cation scavenger which is 1,4,7,10,13,16-hexaoxacyclooctadecane (18-C-6, 50 mol %) in ethanol was added at a flow rate of 0.2 mL min$^{-1}$ and mixed with a stream of oxygen gas (10 mL·min$^{-1}$), affording compound (2-chlorophenyl)(1-hydroxycyclopentyl)methanone (IIIa) in >97% conversion (96% selectivity).

Example 11

Preparation of (2-Chlorophenyl)(1-Hydroxycyclopentyl)Methanone (IIIa) in Flow with Tetramethylammonium Hydroxide as Second Additive A feed solution containing (2-chlorophenyl)(cyclopentyl)methanone (IIa) (1 M), a first additive in the form of a reductant which is triethyl phosphite ((P(OEt)$_3$), 110 mol %) and a second additive in the form of a base which is tetramethylammonium hydroxide (50 mol %) in ethanol was pumped at a flow rate of 0.2 mL min$^{-1}$ and mixed with a stream of oxygen gas (10 mL·min$^{-1}$). Oxygen (AirLiquide, Alphagaz 1) and the liquid feed solution were mixed through a static mixer (T-Mixer, IDEX-Upchurch, natural PEEK 1/4-28 thread for 1/16" o.d. tubing, 0.02" through hole) placed upstream the reaction coil. The resulting reaction mixture was reacted for 5 min in the reaction coil under thermal conditions at 30° C. The continuous-flow setup for the oxygenation of (2-chlorophenyl)(cyclopentyl)methanone (IIa) was constructed from a high purity PFA capillary (800 μm internal diameter) wrapped in coils in a thermoregulated device. A back-pressure regulator set at 160 psi was inserted downstream. The reactor effluent was collected and processed, affording compound (2-chlorophenyl)(1-hydroxycyclopentyl)methanone (IIIa) in >99% conversion (91% selectivity).

Examples 6 to 11 show a superior effect of this reaction step in flow versus this reaction step in batch (cfr examples 2 and 4): the reaction time is drastically reduced to 5 minutes while excellent yield and selectivity are obtained.

Example 12

Preparation of (2-Chlorophenyl)(1-Hydroxycyclopentyl)Methanone (IIIa) in Flow with Photo-Irradiation A feed solution containing (2-chlorophenyl)(cyclopentyl)methanone (IIa) (0.1 M) in ethanol and a second additive containing a base which is cesium carbonate (Cs$_2$CO$_3$) (20 mol %) and a photosensitizer which is Rose Bengal (5 mol %) was pumped at a flow rate of 0.1 mL min$^{-1}$ and mixed with a stream of oxygen gas (10 mL·min$^{-1}$). Oxygen (AirLiquide, Alphagaz 1) and the liquid feed solution were mixed through a static mixer (T-Mixer, IDEX-Upchurch, natural PEEK 1/4-28 thread for 1/16" o.d. tubing, 0.02" through hole) placed upstream the irradiation coil. The resulting reaction mixture was reacted for 15 min in the irradiation coil. The continuous-flow setup for the photocatalytic oxygenation of (2-chlorophenyl)(cyclopentyl)methanone (IIa) was constructed from a high purity PFA capillary (800 μm internal diameter) wrapped in coils around a reflective, thermoregulated aluminum cylinder. The PFA coils were surrounded by 4 adjustable heat-sink integrated pillars each supporting 3 high power LEDs (540 nm, LZ1-00G102, Led Engin). The LEDs were mounted to face towards the PFA coil wrapped around the central cylinder. A back-pressure regulator set at 250 psi was inserted downstream. The reactor effluent was collected, quenched with a first additive which is a reductant in the form of sodium metabisulfite (Na$_2$S$_2$O$_5$) and processed, affording compound (2-chlorophenyl)(1-hydroxycyclopentyl)methanone (IIIa) in 40% conversion.

Compared to example 3 in batch, an increase in conversion was observed for this example in flow with photo-irradiation, together with a drastic reduction of reaction time (15 min versus 10 hours).

Example 13

Preparation of 1-[(2-Chlorophenyl)(Methylimino) Methyl]Cyclopentanol (IVa) in Batch A 250 mL round-bottom flask was charged with 20 g (90 mmol, 1 eq.) of (2-chlorophenyl)(1-hydroxycyclopentyl)methanone (IIIa) and 60 mL (90 mmol, 5 eq.) of a 33 wt.-% solution of a nitrogen-containing nucleophile in the form of methylamine (MeNH$_2$) in absolute ethanol, and hermetically sealed. The resulting mixture was stirred at room temperature for 6 days. The solvent was then removed under reduced pressure, and 1-[(2-chlorophenyl)(methylimino)methyl]cyclopentanol (IVa) was obtained as a pale-yellow solid was obtained (97% yield). Characterization $^1$H NMR (400 MHz, CDCl$_3$) 7.50-7.45 (m, 1H), 7.40-7.31 (m, 2H), 7.11-7.06 (m, 1H), 5.84-5.02 (m, 1H), 3.03 (s, 3H), 2.02-1.86 (m, 4H), 1.85-1.75 (m, 1H), 1.74-1.49 (m, 3H). $^{13}$C NMR (100.6 MHz, CDCl$_3$) 173.0, 134.0, 129.9, 129.8, 128.9, 126.6, 84.3, 39.4, 38.3, 37.9, 23.6, 23.4. ESI-HRMS: [M+H]$^+$ calcd: 238.09932, found: 238.09920.

Example 14

Preparation of 1-[(2-Chlorophenyl)(Methylimino) Methyl]Cyclopentanol (IVa) in Flow A feed solution containing (2-chlorophenyl)(1-hydroxycyclopentyl)methanone (IIIa) (0.36 M) in ethanol was pumped at a flow rate of 0.1 mL min$^{-1}$ and mixed through a static mixer (T-Mixer, IDEX-Upchurch, natural PEEK 1/4-28 thread for 1/16" o.d. tubing, 0.02" through hole) with a stream containing a nitrogen-containing nucleophile in the form of methylamine (MeNH$_2$) in ethanol. The static mixer was placed upstream the reaction coil. The resulting reaction mixture was reacted for 4-15 min in the reaction coil (Table 1). The continuous-flow setup was constructed from a high purity PFA capillary (800 μm internal diameter) wrapped in coils in a thermoregulated device. A back-pressure regulator set at 250 psi was inserted downstream. The reactor effluent was collected and concentrated to afford 1-[(2-chlorophenyl)(methylimino)methyl]cyclopentanol (IVa) in 11-85% conversion.

TABLE 1

| Entry | MeNH$_2$ (equiv.) | Residence time (min) | Temperature (° C.) | Conversion (%) |
|---|---|---|---|---|
| 1 | 10 | 4 | 80 | 11 |
| 2 | 10 | 4 | 100 | 15 |
| 3 | 10 | 4 | 120 | 29 |
| 4 | 5 | 6 | 120 | 33 |
| 5 | 5 | 11 | 120 | 55 |
| 6 | 5 | 15 | 130 | 85 |

Example 15

Preparation of 1-[(2-Chlorophenyl)(Methylimino) Methyl]Cyclopentanol (IVa) in Flow with Triisopropyl Borate as Third Additive A feed solution containing (2-chlorophenyl)(1-hydroxycyclopentyl)methanone (IIIa) (4.48 M) and a third additive in the form of triisopropyl borate (200 mol %) in ethanol was pumped at a flow rate of 0.7 mL min$^{-1}$ and mixed through a static mixer (T-Mixer, IDEX-Upchurch, natural PEEK 1/4-28 thread for 1/16" o.d. tubing, 0.02" through hole) with a stream containing a nitrogen-containing nucleophile in the form of methylamine (MeNH$_2$) in ethanol (33%) injected at a flow rate of 0.8 mL min$^{-1}$. The static mixer was placed upstream the reaction coil. The resulting reaction mixture was reacted for 1 min in the reaction coil at 60° C. The continuous-flow setup was constructed from a high purity PFA capillary (800 μm internal diameter) wrapped in coils in a thermoregulated device. A back-pressure regulator set at 75 psi was inserted downstream. The reactor effluent was collected and concentrated to afford 1-[(2-chlorophenyl)(methylimino)methyl]cyclopentanol (IVa) in 99% conversion.

Examples 14 and 15 show a superior effect of this reaction step in flow versus this reaction step in batch (cfr example 13): the reaction time is drastically reduced while maintaining an excellent yield.

Example 16

Preparation of (R,S)-2-(2-Chlorophenyl)-2-(Methylamino)Cyclohexanone, (R,S)-Ketamine Free Base (rac-1) Under Microwave Irradiation as a Mimic of Continuous Flow Conditions 5 mL of a solution of 1-[(2-chlorophenyl)(methylimino)methyl]cyclopentanol (IVa) in absolute ethanol (0.42 M) was heated at temperatures ranging from 140 to 180° C. under microwave irradiation in a 20 mL batch vial for reaction times ranging from 2.5 to 30 min under 20 bar of pressure (Table 2) in the presence of a fourth additive in the form of a heterogeneous acid catalyst (Montmorillonite K10). The reaction mixture was filtered and the solvent was evaporated, affording (R,S)-ketamine rac-1 free base in 23-81% conversion (99% selectivity). Characterization $^1$H NMR (400 MHz, CDCl$_3$) 7.55 (dd, J=7.8, 1.7 Hz, 1H), 7.38 (dd, J=7.8, 1.5 Hz, 1H), 7.32 (td, J=7.6, 1.5 Hz, 1H), 7.28-7.21 (m, 1H), 2.87-2.70 (m, 1H), 2.59-2.41 (m, 2H), 2.11 (s, 3H), 2.00 (ddt, J=12.1, 6.9, 4.8 Hz, 1H), 1.94-1.81 (m, 1H), 1.81-1.68 (m, 3H). $^{13}$C NMR (100.6 MHz, CDCl$_3$) 209.2, 137.9, 133.8, 131.2, 129.4, 128.7, 126.6, 70.2, 39.6, 38.7, 29.1, 28.1, 21.9. ESI-HRMS: [M+H]$^+$ calcd: 238.09932, found: 238.09936.

TABLE 2

| Entry | Catalyst (loading in mol %) | Residence time (min) | Temperature (° C.) | Conversion (%) | Selectivity (%) |
|---|---|---|---|---|---|
| 1 | K10 (100) | 15 | 140 | 23 | 99 |
| 2 | K10 (100) | 15 | 160 | 56 | 99 |
| 3 | K10 (100) | 15 | 180 | 81 | 99 |
| 4 | K10 (100) | 30 | 180 | 80 | 99 |
| 5 | / | 15 | 180 | 43 | 99 |

Example 17

Preparation of (R,S)-2-(2-Chlorophenyl)-2-(Methylamino)Cyclohexanone, (R,S)-Ketamine Free Base (rac-1) in Flow A solution of 1-[(2-chlorophenyl)(methylimino)methyl] cyclopentanol (IVa) in absolute ethanol (0.36 M) was injected at a flow rate of 0.1 mL min$^{-1}$ with a HPLC pump toward a stainless steel microfluidic reactor loop (2.5 mL internal volume, corresponding to a residence time of 25 min). The reactor was operated under thermal conditions at 180° C. under 250 psi of counter-pressure. The reactor effluent was collected and processed, affording (R,S)-ketamine rac-1 free base in 30% yield.

Example 18

Preparation of (R,S)-2-(2-Chlorophenyl)-2-(Methylamino)Cyclohexanone, (R,S)-Ketamine Free Base (rac-1) in Flow, with Toluene as an Alternative Solvent A solution of 1-[(2-chlorophenyl)(methylimino)methyl] cyclopentanol (IVa) in toluene (0.36 M) was injected at a flow rate of 0.1 mL min$^{-1}$ with a HPLC pump toward a stainless steel microfluidic reactor loop (2.5 mL internal volume, corresponding to a residence time of 25 min). The reactor was operated at various temperatures under 1000 psi of counter-pressure (Table 3). The reactor effluent was collected and processed, affording (R,S)-ketamine rac-1 free base in 12-70% yield.

TABLE 3

| Entry | Residence time (min) | Temperature (° C.) | Yield (%) |
|---|---|---|---|
| 1 | 25 | 180 | 12 |
| 2 | 25 | 200 | 30 |
| 3 | 25 | 220 | 70 |

TABLE 3-continued

| Entry | Residence time (min) | Temperature (° C.) | Yield (%) |
|---|---|---|---|
| 4 | 25 | 240 | decomposition |
| 5 | 25 | 260 | decomposition |
| 6 | 5 | 260 | decomposition |

Example 19

Preparation of (R,S)-2-(2-Chlorophenyl)-2-(Methylamino)Cyclohexanone, (R,S)-Ketamine Free Base (rac-1) in Flow, with Montmorillonite K10 as Fourth Additive 1 L of 1-[(2-chlorophenyl)(methylimino)methyl]cyclopentanol (IVa) in ethanol (0.42 M) was pumped at a flow rate of 0.8 mL min$^{-1}$ was reacted at 180° C. for a residence time of 15 min in a stainless steel column packed with 3.7 of Montmorillonite K10 as a heterogeneous catalyst. The reactor was operated at various temperatures under 500 psi of counter-pressure (Table 2). The reactor effluent was collected and processed, affording (R,S)-ketamine rac-1 free base in 75% conversion and >99% selectivity. Compared to example 16 under microwave irradiation, the flow conditions enable treatment of a much higher volume of sample (up to 1 L and even up to 10 L without restrictions).

Example 20

Preparation of (R,S)-2-(2-Chlorophenyl)-2-(Methylamino)Cyclohexanone, (R,S)-Ketamine Free Base (rac-1) in Flow, Telescoping Two Steps A feed solution containing (2-chlorophenyl)(1-hydroxycyclopentyl)methanone (IIa) (0.36 M) in ethanol was pumped at a flow rate of 0.1 mL min$^{-1}$ and mixed through a static mixer (T-Mixer, IDEX-Upchurch, natural PEEK 1/4-28 thread for 1/16" o.d. tubing, 0.02" through hole) with a stream containing a nitrogen-containing nucleophile in the form of methylamine (MeNH$_2$) in ethanol. The static mixer was placed upstream the reaction coil. The resulting reaction mixture was reacted for 15 min in the reaction coil operated at 130° C. The continuous-flow setup was constructed from a stainless steel tubing (500 μm internal diameter) wrapped in coils. The reactor effluent was next conveyed to a second reaction coil operated at 180° C. The second reaction coil was constructed from stainless steel tubing (500 μm internal diameter) wrapped in coils (2.5 mL internal volume, corresponding to a total residence time of 15 min). A back-pressure regulator set at 500 psi was inserted downstream. The crude effluent was collected and analyzed. It contained 63% of compound 1-[(2-chlorophenyl)(methylimino)methyl]cyclopentanol (IVa), 7% of rac-ketamine and 30% of unreacted (2-chlorophenyl)(1-hydroxycyclopentyl)methanone (IIIa).

This example highlights the superiority of flow versus batch because of its possibility to successfully telescoping two reaction steps into one.

Example 21

Preparation of (R,S)-2-(2-Chlorophenyl)-2-(Methylamino)Cyclohexanone Hydrochloride, ((R,S)-Ketamine Hydrochloride, rac-1.HCl) in Batch in Ethanol A solution of 1-[(2-chlorophenyl)(methylimino)methyl]cyclopentanol (IVa) in absolute ethanol (0.42 M) was heated at 170° C. under microwave irradiation in a 20 mL batch vial for 15 min under 20 bar of pressure (Table 2) in the presence of a fourth additive in the form of a homogeneous acid catalyst (HCl in ethanol 1M). The reaction mixture was evaporated, affording (R,S)-ketamine hydrochloride, rac-1.HCl in 54% conversion and 50% selectivity.

Example 22

Preparation of (R,S)-2-(2-Chlorophenyl)-2-(Methylamino)Cyclohexanone Hydrochloride, (R,S)-Ketamine Hydrochloride, rac-1.HCl) in Batch in O-Dichlorobenzene A solution of 1-[(2-chlorophenyl)(methylimino)methyl]cyclopentanol (IVa) (2.00 g, 8.41 mmol, 1 eq.) was dissolved in 20 mL of o-dichlorobenzene in the presence of 2.11 mL (8.44 mmol, 2 eq.) of dioxane solution of hydrochloric acid, and the resulting mixture was refluxed for 30 min in a round-bottom flask equipped with a condenser. The mixture was allowed to cool down to room temperature, and a white precipitate was collected. The solid was filtrated and washed with 50 mL of diethyl ether. (R,S)-ketamine hydrochloride (rac-1.HCl) was obtained with 74% yield (>99% selectivity). Characterization $^1$H NMR (400 MHz, D$_2$O) 7.86-7.73 (m, 1H), 7.52 (d, J=5.9 Hz, 3H), 3.36-3.15 (m, 1H), 2.46 (dd, J=11.7, 6.1 Hz, 2H), 2.33 (s, 3H), 2.01 (dt, J=16.5, 3.8 Hz, 1H), 1.90-1.74, (m, 2H), 1.64 (dtt, J=16.4, 13.1, 4.3 Hz, 2H). $^{13}$C NMR (100.6 MHz, D$_2$O) 211.1, 132.8, 132.0, 131.8, 72.6, 39.5, 36.2, 30.1, 27.1, 21.2. ESI-HRMS: [M+H]$^+$ calcd: 238.09932, found: 238.09946.

Example 23

Preparation of (R,S)-2-(2-Chlorophenyl)-2-(Methylamino)Cyclohexanone Hydrochloride, (R,S)-Ketamine Hydrochloride, rac-1.HCl) in Flow A solution of 1-[(2-chlorophenyl)(methylimino)methyl]cyclopentanol (IVa) in absolute ethanol (0.36 M) was pumped at a flow rate of 0.24 mL min$^{-1}$ with a HPLC pump, and a solution of a fourth additive in the form of a pharmaceutically acceptable acid which is HCl in absolute ethanol (0.9 M) was pumped at a flow rate of 0.16 mL min$^{-1}$ with a metal-free HPLC pump. Both streams were mixed through a static PEEK T-mixer, and next reacted in a microfluidic reactor loop constructed from a PFA capillary embed in a copper coil (2 mL internal volume, corresponding to a residence time of 5 min). The reactor was operated at 175° C. under 250 psi of counter-pressure. The reactor effluent was collected and processed, affording (R,S)-ketamine hydrochloride (rac-1.HCl) in 70% yield (>99% purity, HPLC). This example shows the superior effect of this reaction step in flow versus this reaction step in batch (cfr examples 21 and 22) with an increase in the purity of the product obtained.

What is claimed is:

1. A method for synthesizing a compound of formula

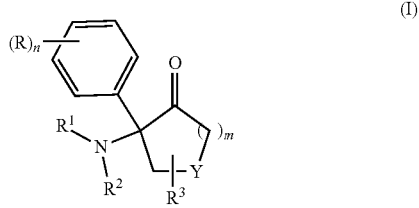

(I)

wherein each R independently represents an optionally substituted aryl, heteroaryl, alkyl, perfluoroalkyl, cycloalkyl, alkoxy, aryloxy, acyl, carboxyl, hydroxyl, halogen, amino, nitro, cyano, sulfo or sulfhydryl group, in ortho, meta or para position to the cycloalkylamine moiety;

$R^1$ represents a hydrogen atom or a lower alkyl group;

R2 represents a hydrogen atom;

$R^3$ represents a hydrogen group, substituted aryl, heteroaryl, alkyl, perfluoroalkyl, cycloalkyl, alkoxy, aryloxy group;

Y represents an oxygen atom, a sulfur atom, a NH group, a $NR^4$ group or a $CH_2$ group;

$R^4$ represents a hydrogen atom or an alkyl, aryl or a heteroaryl group;

n and m each independently represents an integer from 1 to 5;

or a pharmaceutically acceptable salt thereof; or a precursor thereof; wherein the method comprises step (c), or step (c) and at least one or more of the following steps (a) and (b): (a) reacting a compound of formula (II)

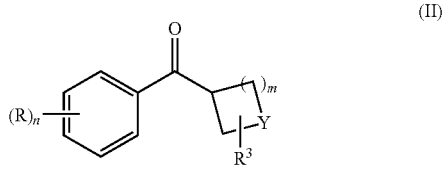

(II)

wherein R, $R^3$, Y, n and m are as defined above in relation to the compound of formula (I) with an oxygenating agent, a first additive, and a second additive in a solvent in a fluidic network or in a batch process under thermal and/or photochemical conditions to form a compound of formula (III)

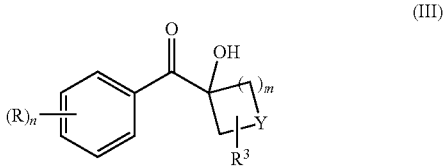

(III)

wherein R, $R^3$, Y, n and m are as defined above in relation to the compound of formula (I), (b) reacting a compound of formula (III) with a nitrogen containing nucleophile in the presence of a third additive and/or a solvent in the fluidic network or in a batch process under thermal conditions to form a compound of formula (IV)

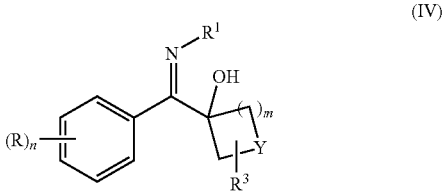

(IV)

wherein R, $R^1$, $R^3$, Y, n and m are as defined above in relation to the compound of formula (I); and/or (c) reacting a compound of formula (IV) in a fluidic network, optionally in the presence of a fourth additive, under thermal conditions to form a compound of formula (I) substantially free from impurities;

wherein one or more of steps (a) and (b) is carried out in a fluidic network; wherein a fluidic network comprises one or more micro- and/or meso-channels having an internal dimension of from 100 μm to 2000 μm; wherein a lower alkyl group is a saturated optionally substituted straight- or branched-chain hydrocarbon containing from 1 to 4 carbon atoms.

2. The method as defined in claim 1 wherein the fluidic network comprises transparent micro- and/or meso-channels where step (a) is carried out under photochemical conditions.

3. The method as defined in claim 1 wherein one or more of the steps comprises one or more of the following steps: (i) flowing a fluid sample into a micro-/meso-channel; and/or (ii) performing an in-line purification; and/or (iii) performing an in-line analysis; and/or (iv) performing a chemical reaction in the micro-/meso-channel.

4. The method as defined in claim 1 wherein step (a) comprises reacting a compound of formula (II) with an oxygenating agent, a first additive and a second additive which is a base in a solvent under thermal conditions to form a compound of formula (III).

5. The method as defined in claim 1 wherein step (a) comprises reacting a compound of formula (II) with an oxygenating agent, a first additive and a second additive which is a catalyst in a solvent in a fluidic network under photochemical conditions to form a compound of formula (III).

6. The method as defined in claim 1 wherein step (a) is telescoped to step (b).

7. The method as defined in claim 1 wherein steps (a), (b), and (c) are carried out in a fluidic network that comprises micro- and/or meso-channels.

8. The method as defined in claim 1 wherein step (c) comprises flowing a fluid sample comprising a compound of formula (IV) into a micro-/meso-channel; and/or performing an in-line purification of the compound of formula (IV); and/or performing an in-line analysis of the compound of formula (IV); and/or performing a chemical reaction, in the micro-/meso-channel, to convert the compound of formula (IV) to the compound of formula (I).

9. The method as defined in claim 1 wherein step (b) further comprises a dehydration reagent.

10. The method as defined in claim 1 wherein step (b) is carried out at a temperature from 60° C. to 180° C.

11. The method as defined in claim 1 wherein step (b) is telescoped to step (c).

12. The method as defined in claim 1 wherein step (c) comprises a fourth additive which is an acid.

13. The method as defined in claim 1 wherein step (c) is carried out at a temperature of from 160° C. to 260° C.

14. The method as defined in claim 1 wherein step (c) is telescoped to a subsequent process operation.

15. The method as defined in claim 1 wherein step (c) is telescoped to a subsequent chemical transformation.

16. The method as defined in claim 1 wherein step (c) reacting the compound of formula (IV) in a solvent which is an alcohol in which the solubility of a pharmaceutically acceptable salt of a compound of formula (I) can be altered either by cooling or by adding an antisolvent.

17. The method as defined in claim 7 wherein the method comprises a continuous-flow method for synthesizing a compound of formula (I).

18. The method as defined in claim 14 wherein step (c) is telescoped to a subsequent process operation such that step (c) additionally comprises a step of an in- or off-line downstream purification including quench, liquid-liquid extraction, liquid-liquid separation, gas-liquid separation, filtration on silica gel or in-line crystallization.

19. The method as defined in claim 15 wherein step (c) additionally comprises a step of:
reacting a compound of formula (I) with a pharmaceutically acceptable acid to form a pharmaceutically acceptable salt of a compound of formula (I), or an analog thereof;
reacting a compound of formula (I) with an organic and/or inorganic base or acid to increase the amount of a specific stereoisomer of the compound of formula (I).

20. The method as defined in claim 16 wherein step (c) additionally comprises a step of:
injection of a solution comprising a pharmaceutically acceptable acid to react with a free base of formula (I), such that a salt of the said acid and the compound of formula (I) is formed;
injection of antisolvent in a section of fluidic network comprising a micro- and/or meso-channel to crystallize a pharmaceutically acceptable acid to form a salt of a compound of formula (I), or an analog thereof; and/or
flowing a salt of a compound of formula (I) in a section of fluidic network comprising a micro- and/or meso-channel in which the temperature is decreased from an initial value to a target lower temperature.

21. The method as defined in claim 16 wherein the antisolvent is an ether, an oxygenous heterocycle, an alkane, or a cycloalkane.

22. The method as defined in claim 16 wherein the pharmaceutically acceptable salt of a compound of formula (I) is a hydrochloride salt.

* * * * *